US007803586B2

(12) United States Patent
Brown et al.

(10) Patent No.: US 7,803,586 B2
(45) Date of Patent: Sep. 28, 2010

(54) CHEMICAL PROCESS

(75) Inventors: David Brown, Bristol (GB); John Peter Gilday, Bristol (GB); Philip Anthony Hopes, Bristol (GB); Jonathan David Moseley, Bristol (GB); Evan William Snape, Bristol (GB); Andrew Wells, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 546 days.

(21) Appl. No.: 11/793,134

(22) PCT Filed: Dec. 14, 2005

(86) PCT No.: PCT/GB2005/004800

§ 371 (c)(1),
(2), (4) Date: Jun. 14, 2007

(87) PCT Pub. No.: WO2006/064213

PCT Pub. Date: Jun. 22, 2006

(65) Prior Publication Data

US 2008/0115247 A1 May 15, 2008

(30) Foreign Application Priority Data

Dec. 16, 2004 (GB) .................................. 0427524.4

(51) Int. Cl.
*C12P 7/40* (2006.01)
*C12P 11/00* (2006.01)

(52) U.S. Cl. ...................................... 435/136; 435/130
(58) Field of Classification Search ..................... None
See application file for complete search history.

(56) References Cited

FOREIGN PATENT DOCUMENTS

| WO | WO 01/11072 | 2/2001 |
| WO | WO 01/11073 | 2/2001 |
| WO | WO 03/051826 | 6/2003 |
| WO | WO 2004/113282 | 12/2004 |
| WO | WO 2004/113283 | 12/2004 |
| WO | WO 2004/113284 | 12/2004 |
| WO | WO 2004/113285 | 12/2004 |

OTHER PUBLICATIONS

Haigh et al. "Non-thiazolidinedione Antihyperglycaemic Agents. Part 3: The effects of stereochemistry on the potency of α-methoxy-β-phenylpropanoic acids" Bioorganic and Medicinal Chemistry 7: 821-830 (1999).
Zhu, J., et al.: "Synthesis of Optically Pure (S)-2-Acetylthio-3-Benzenepropanoic Acid Via Enzymatic Resolution", Tetrahedron Letters, Elsevier, vol. 43(42), pp. 7585-7587, 2002.

*Primary Examiner*—Nashaat T Nashed
(74) *Attorney, Agent, or Firm*—Morgan Lewis & Bockius LLP

(57) ABSTRACT

Enzymatic and chemical processes for the preparation of certain of 3-phenyl-2-arylalkylthiopropionic acid derivatives which have utility in treating clinical conditions including lipid disorders (dyslipidemias) whether or not associated with insulin resistance and other manifestations of the metabolic syndrome are described and also certain novel intermediates used in these processes.

8 Claims, No Drawings

CHEMICAL PROCESS

The present invention relates to processes for the preparation of certain of 3-phenyl-2-arylalkylthiopropionic acid derivatives which have utility in treating clinical conditions including lipid disorders (dyslipidemias) whether or not associated with insulin resistance and other manifestations of the metabolic syndrome. The invention also relates to certain novel intermediates used in this process.

WO 03/051826 discloses compounds of formula A

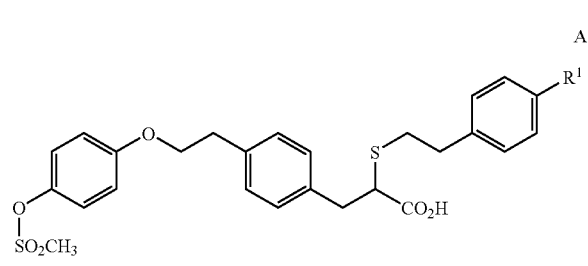

wherein $R^1$ represents chloro, fluoro or hydroxy as well as optical isomers and racemates thereof as well as pharmaceutically acceptable salts, prodrugs, solvates and crystalline forms thereof which are selective PPARα modulators. These compounds are useful in treating clinical conditions including lipid disorders (dyslipidemias) whether or not associated with insulin resistance and other manifestations of the metabolic syndrome. Certain processes for the preparation of compounds of formula A are disclosed in this document. Improved processes for the preparation of compounds of formula A have now been found. Related compounds are disclosed in co-pending applications WO2004/113282, WO2004/113283 and WO2004/113284. A racemisation process is disclosed in co-pending application WO2004/113285.

Selective *Rhizopus delemar* lipase catalysed ester hydrolysis of methyl 3-[4-[2-[N-(2-benzoxazolyl)-N-methylamino] ethoxy]phenyl]-2-methoxypropanoate that produces resolved acid is disclosed in Bioorganic and Medicinal Chemistry 7 (1999) 821-830.

Selective enzymatic hydrolysis of 2-alkoxy-3-(4-hydroxyphenyl)propanoic acid esters is described in WO 01/11072 and WO 01/11073.

Synthesis of optically pure (S)-2-acetylthio-3-benzenepropanoic acid via enzymic resolution is disclosed in Tetrahedron Letters 43 (42) 7585-7587, 2002.

However, it cannot be predicted in advance which enzymes will produce a selective hydrolysis of a particular ester substrate and which will not. This is especially true of substrates with a high degree of branching at the carbon α to the carboxyl function. It has surprisingly been found that certain enzymes are useful in the hydrolysis of esters to produce the compounds disclosed in WO 03/051826 in high enantiomeric purity.

The present invention provides a process for the preparation of an enantiomerically enriched compound of formula I and pharmaceutically acceptable salts thereof

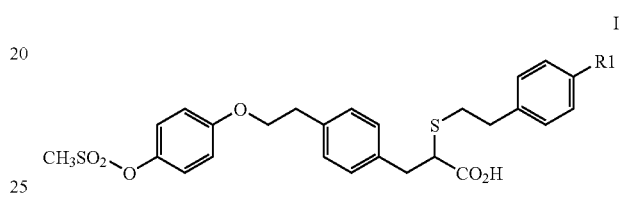

in which $R^1$ represents chloro, fluoro or hydroxy which comprises hydrolysing a compound of formula II

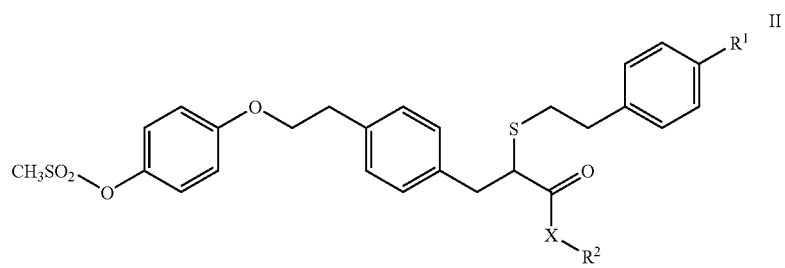

in which $R^1$ is as initially defined, X is O or S and $R^2$ is a $C_{1-10}$alkyl group, a $C_{1-6}$haloalkyl, a $C_{2-6}$alkenyl group, aryl, an aryl$C_{1-6}$alkylene group, with or without additional hetero substitution with an enzyme selected from a) *Mucor miehei* lipase, *Candida rugosa* lipase, *Candida cylindracia* lipase, *Thermomyces lanuginosa* lipase, *Mucor javanicus* lipase and *Rhizopus delemar* lipase when X is O or b) *Pseudomonas cepacia* lipase when X is S; in the presence of a reaction medium at a temperature in the range of 10-60° C., preferably in the range 20-40° C.

The term with additional hetero substitution means that the alkyl and alkylene groups in $R^2$ may interrupted by nitrogen or oxygen thus providing amino and ether linkages in $R^2$. In one embodiment $R^2$ is a $C_{1-10}$alkyl group, a $C_{1-6}$haloalkyl, aryl, an aryl$C_{1-6}$alkylene group, with or without additional hetero substitution. In another embodiment $R^2$ is a $C_{1-10}$alkyl group, a $C_{1-6}$haloalkyl, aryl or an aryl$C_{1-6}$alkylene group.

In a further aspect the present invention provides a process for the preparation of an enantiomerically enriched compound of formula I and pharmaceutically acceptable salts thereof

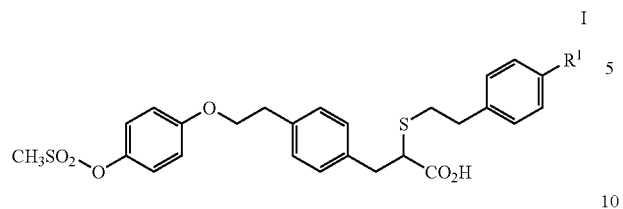

in which R[1] represents chloro, fluoro or hydroxy which comprises hydrolysing a compound of formula II

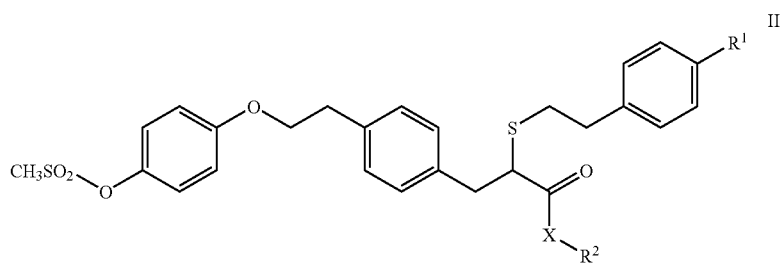

in which R[1] is as initially defined, X is O and R[2] is a $C_{1-10}$alkyl group with an enzyme selected from *Mucor miehei* lipase, *Candida rugosa* lipase, *Candida cylindracia* lipase *Thermomyces lanuginosa* lipase, *Mucor javanicus* lipase and *Rhizopus delemar* lipase when X is O in the presence of a reaction medium.

In a still further aspect the present invention provides a process for the preparation of an enantiomerically enriched compound of formula I or a pharmaceutically acceptable salt thereof

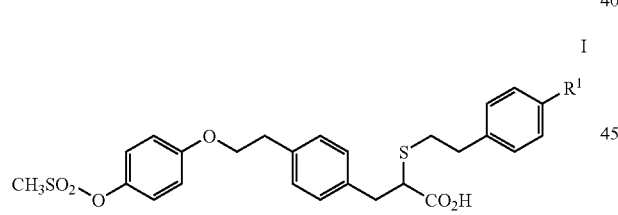

in which R[1] represents chloro, fluoro or hydroxy which comprises hydrolysing a compound of formula II in which R[1] is as initially defined, X is S and R[2] is a $C_{1-10}$alkyl group with *Pseudomonas cepacia* lipase in the presence of a reaction medium.

In another aspect the invention provides a process for the preparation of a compound of formula III or a pharmaceutically acceptable salt thereof

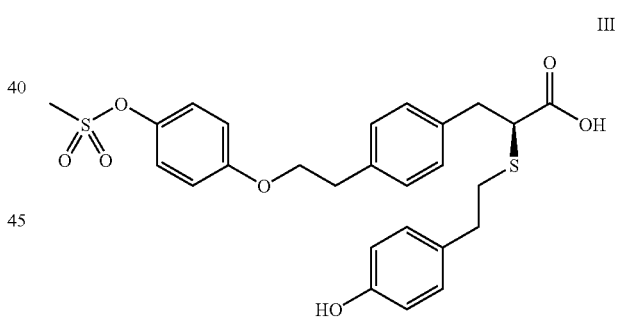

comprising reacting a compound of formula IV

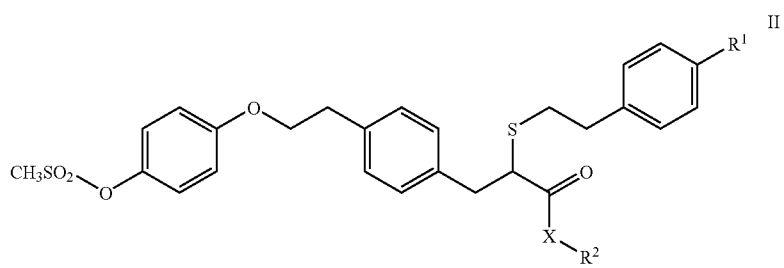

IV

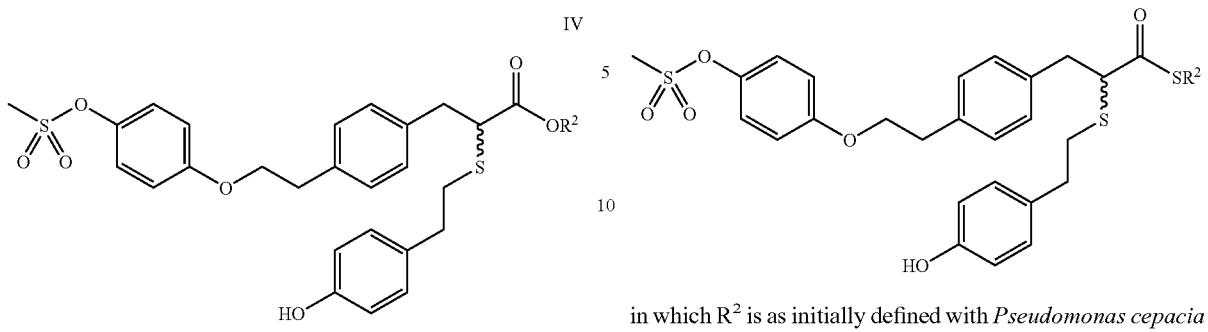

in which R² is as initially defined with a lipozyme selected from *Mucor miehei* lipase, *Candida rugosa* lipase, *Candida cylindracia* lipase, *Thermomyces lanuginosa* lipase, *Mucor javanicus* lipase and *Rhizopus delemar* lipase in a reaction medium.

In another aspect the invention provides a process for the preparation of a compound of formula III or a pharmaceutically acceptable salt thereof

III

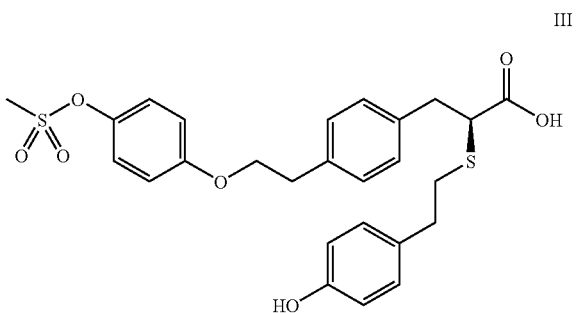

comprising reacting a compound of formula V

V

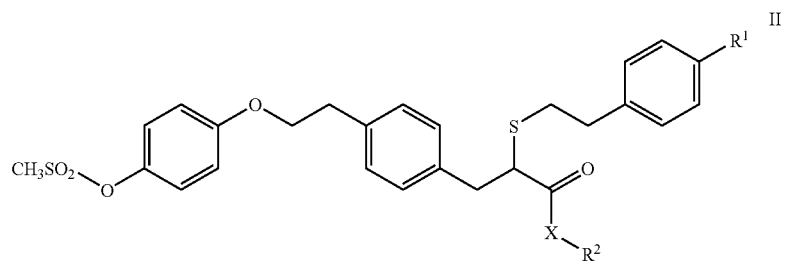

in which R² is as initially defined with *Pseudomonas cepacia* lipase in a reaction medium.

Esters of formula I when treated with suitable hydrolytic enzymes undergo preferential reaction of the (S)-isomer to produce the corresponding (S)-acid or a new (S)-ester thereby effecting an efficient separation of the (S)-enantiomer. Unreacted (R)-esters can be recovered, racemised and recycled. In some cases, dynamic kinetic resolution is possible in which the (R)-ester is racemised and recycled 'in situ'.

The enzyme is a protein capable of enantioselective hydrolysis such as a lipase, esterase, amidase or protease. The enzyme can be used as a pure liquid or solid, diluted with inert carriers, supported on an inert matrix (e.g. macroporous polymer, ion exchange resin, Celite®, ceramic), or used as an inert insoluble preparation (e.g. Cross-linked enzyme crystal (CLEC) or Cross-linked enzyme aggregate (CLEA)), as an encapsulated formulation or attached to, or within, a membrane.

The reaction medium can be water, water-solvent mixtures, solvent-solvent mixtures either mono or bi-phasic containing buffer salts or added bases, or more specialised media like ionic liquids or super-critical carbon dioxide ($SC-CO_2$). Examples of suitable solvents include $C_{1-6}$alkanols (for example propanol, isopropanol, butanol, tert-butanol, pentanol, amyl alcohol or isoamyl alcohol), acetone, methylisobutyl ketone, tetrahydrofuran or acetonitrile.

The preferred reaction medium is a mixture of organic solvent and water which aids solubility and increases the enantioselectivity of the enzyme.

In one aspect the *Pseudomonas cepacia* lipase is a CLEC (Cross-linked enzyme crystal).

The present invention also provides a process for the preparation of an enantiomerically enriched compound of formula II

II

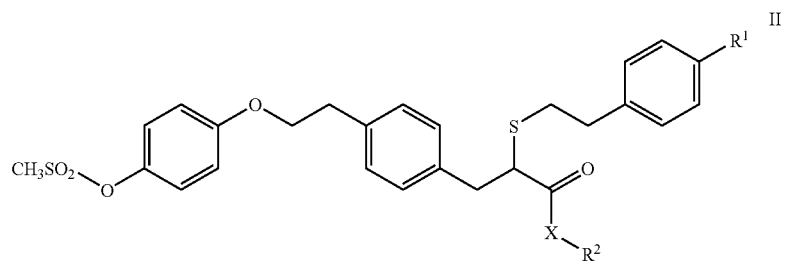

in which R¹ represents chloro, fluoro or hydroxy, X represents O or S and R² represents a $C_{1-6}$alkyl group, a $C_{2-6}$alkenyl group or a phenyl$C_{1-6}$alkyl group, for example a group selected from n-butyl, n-propyl, n-octyl, allyl or benzyl which comprises transesterifying a compound of formula II

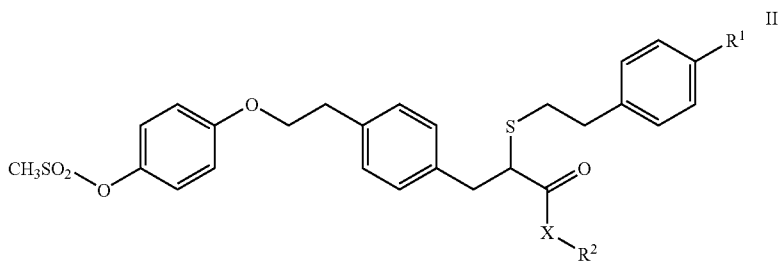

in which R¹ is as initially defined, X is O or S and R² is a C$_{1-6}$alkyl or haloalkyl with or without alkene unsaturation with an enzyme selected from a) *Mucor miehei* lipase, *Candida rugosa* lipase, *Thermomyces lanuginosa* lipase, *Mucor javanicus* lipase and *Rhizopus delemar* lipase when X is O or b) *Pseudomonas cepacia* lipase when X is S; in the presence of a C$_{1-6}$alkanol, a C$_{2-6}$alkenol or a phenylC$_{1-6}$alkanol, respectively, for example n-butanol, n-propanol, n-octanol, prop-2-en-1-ol or benzyl alcohol, respectively, and optionally in the presence of a reaction medium at a temperature in the range of 10-50° C., preferably in the range 20-40° C.

In another aspect the present invention provides a process for the preparation of an enantiomerically enriched compound of formula IVa

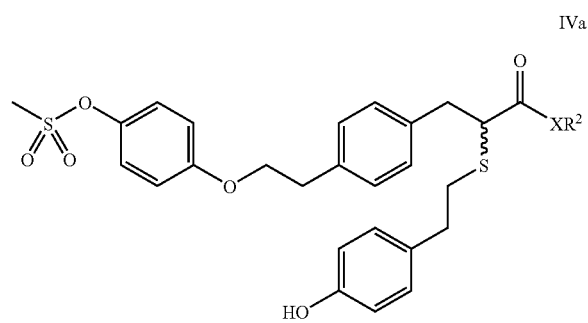

in which X is O or S and R² represents is a C$_{1-6}$alkyl or haloalkyl with or without alkene unsaturation n-butyl which comprises transesterifying a compound of formula IVb

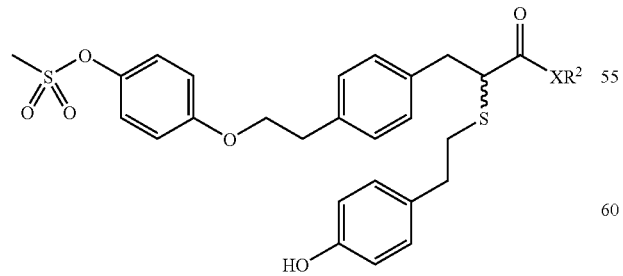

in which R² is a C$_{1-2}$alkyl group with CLEC *Pseudomonas cepacia* lipase in the presence of n-butanol in the presence of a base, for example trioctylamine or other tertiary amines with a similar pKa e.g triethylamine or tributylamine, either as liquids or solid-supported versions and optionally in the presence of a reaction medium at a temperature in the range of 10-50° C., preferably in the range 20-40° C.

The enantiomerically enriched compounds of formula II and IVa may be converted into a enantiomerically enriched compound of formula I by hydrolysis using conditions under which the chiral centre will not racemise for example acid or mild base hydrolysis, hydrolysis with a suitable hydrolytic enzyme, cleavage with Lewis acids, or other ways reported for the mild cleavage of esters, e.g Pd for allyl esters, hydrogenation for benzyl esters.

An alternative approach is to utilise a hydrolytic enzyme working in reverse and chirally esterify the racemic acid with a suitable alcohol-, for example methanol, n-propanol, n-butanol, prop-2-en-1-ol or benzyl alcohol. The chiral acid and ester can be separated and the ester may be cleaved as above.

In one aspect the present invention provides a process for the preparation of a compound of formula I which comprises the steps of a) reacting a compound of formula VI

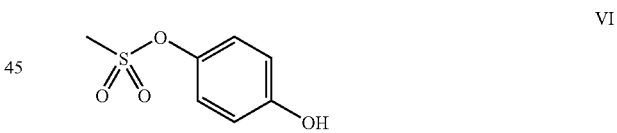

with a compound of formula VII

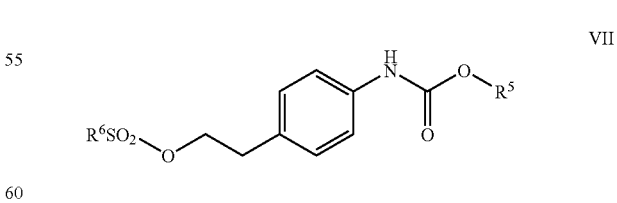

in which R⁵ represents a C$_{1-6}$alkyl group and R⁶ represents p-tolyl in an inert solvent for example acetonitrile and/or toluene, in the presence of a base for example potassium carbonate or sodium carbonate at a temperature in the range of 0° C. to 150° C. to give a compound of formula VIII

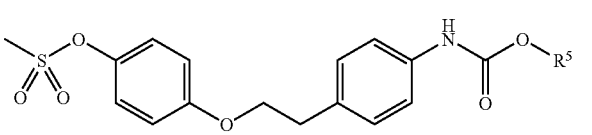

in which R⁵ is as initially defined b) reacting a compound of formula VIII with an acid HA wherein HA represents HCl, HBr or trifluoroacetic acid to give a salt of formula IX

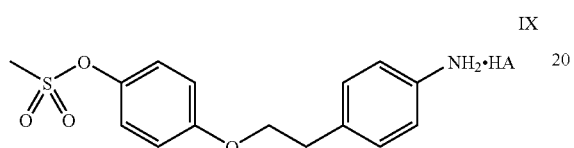

in which HA is as initially defined c) diazotising a compound of formula IX in the presence of hydrochloric acid to give a diazonium salt solution at a temperature in the range of −5° C. to 10° C. and reacting the diazonium salt solution with acrylic acid in an aqueous reaction medium optionally in the presence of a catalyst, for example a copper (I) salt e.g. copper (I) iodide, and reacting the product obtained with ammonia to give a compound of formula X

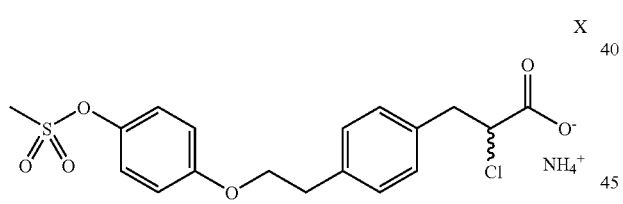

d) reacting a compound of formula X with an acid and then with an alcohol of formula R²OH optionally in the presence of a water scavenging system for example concentrated sulphuric acid or an ortho ester e.g. trimethyl orthoformate or triethyl orthoformate or azeotropic distillation to give a compound of formula XI

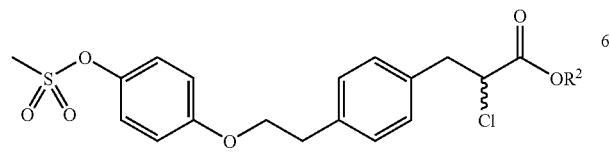

in which R² is as initially defined e) reacting the ester of formula XI with a compound of formula XII

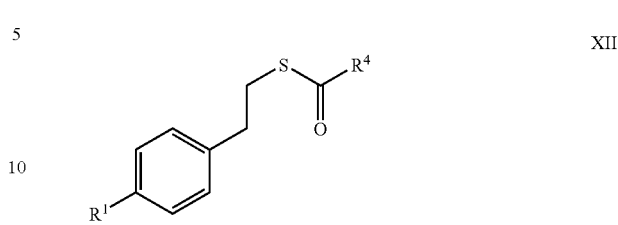

in which R¹ is as initially defined and R⁴ is methyl or phenyl in the presence of a base, for example sodium methoxide, to give a compound of formula XIII

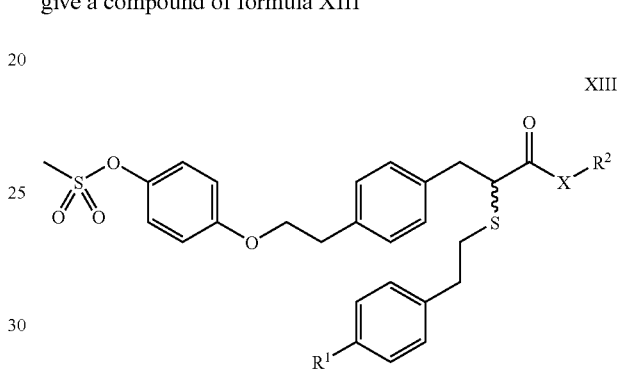

in which R¹, R² and X are as initially defined and f) reacting a compound of formula XIII with an enzyme selected from a) *Mucor miehei* lipase, *Candida rugosa* lipase, *Candida cylindracia* lipase, *Thermomyces lanuginosa* lipase, *Mucor javanicus* lipase and *Rhizopus delemar* lipase when X is O or b) *Pseudomonas cepacia* lipase when X is S in a suitable reaction medium at a temperature in the range of 10-50° C., preferably in the range 20-40° C. to give a compound of formula I

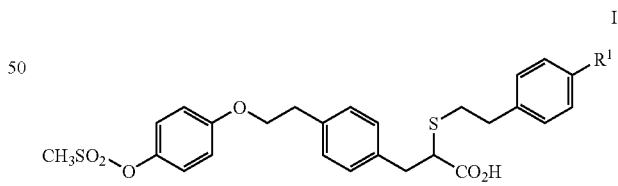

which is enantiomerically enriched and g) optionally reacting the compound of formula I with tert-butylamine in a suitable reaction medium to give the tert-butylammonium salt of the compound of formula I.

In another aspect the present invention provides a process for the preparation of a compound of formula III which comprises the steps of a) reacting a compound of formula VI

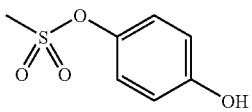

with a compound of formula VII

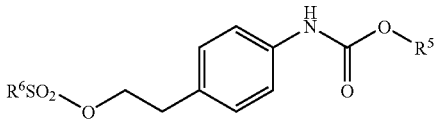

in which $R^5$ represents a $C_{1-6}$alkyl group and $R^6$ represents p-tolyl in an inert solvent for example acetonitrile and/or toluene, in the presence of a base for example potassium carbonate or sodium carbonate at a temperature in the range of 20° C.-150° C. to give a compound of formula VIII

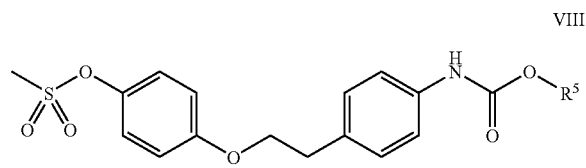

in which $R^5$ is as initially defined b) reacting a compound of formula VIII with trifluoroacetic acid (TFA) to give a salt of formula IX

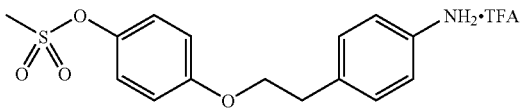

c) diazotising a compound of formula IX in the presence of hydrochloric acid to give a diazonium salt solution at a temperature in the range of −5° C. to 10° C. and reacting the diazonium salt solution with acrylic acid in an aqueous reaction medium optionally in the presence of a catalyst, for example a copper (I) salt e.g. copper (I) iodide, and reacting the product obtained with ammonia to give a compound of formula X

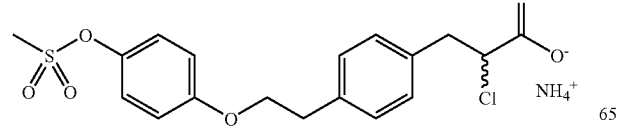

d) reacting a compound of formula X with an acid and then with an alcohol of formula $R^2XH$ optionally in the presence of a water scavenging system for example concentrated sulphuric acid or an ortho ester e.g. trimethyl orthoformate or azeotropic distillation to give a compound of formula XI

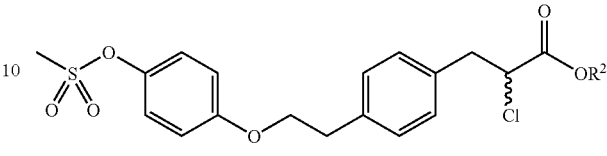

in which $R^2$ is as initially defined e) reacting the ester of formula XI with a compound of formula XIIa

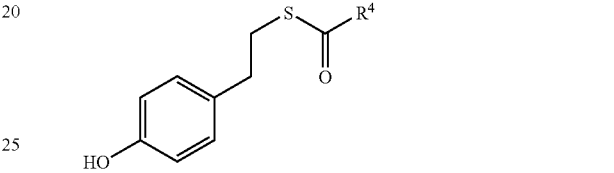

in which $R^1$ is as initially defined and $R^4$ is methyl or phenyl in the presence of a base for example sodium methoxide to give a compound of formula XIIIa

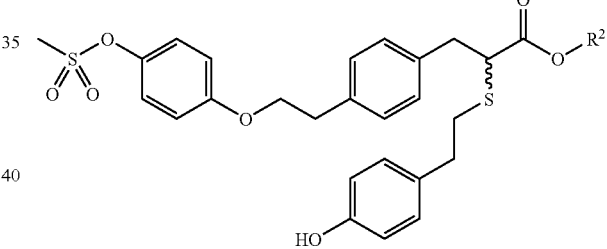

in which $R^2$ is as initially defined and f) reacting a compound of formula XIIIa with an enzyme selected from a) *Mucor miehei* lipase, *Candida rugosa* lipase, *Candida cylindracia* lipase, *Thermomyces lanuginosa* lipase, *Mucor javanicus* lipase and *Rhizopus delemar* lipase; to give a compound of formula III

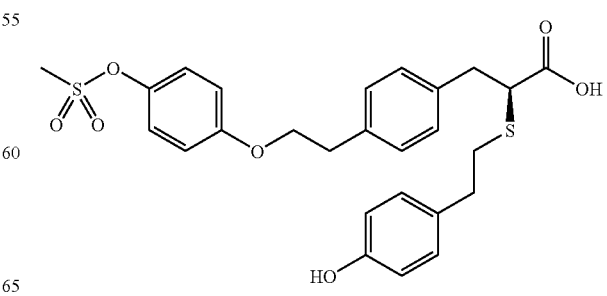

and optionally g) reacting the compound of formula III with tert-butylamine in a suitable reaction medium for example in the presence of an inert solvent to give the tert-butylammonium salt of the compound of formula III.

In another aspect the present invention provides a telescoped process comprising the steps of a) reacting a compound of formula X

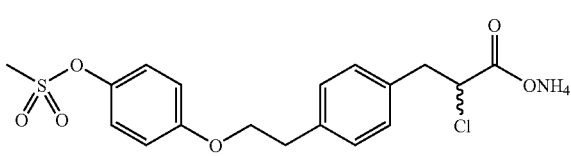

X with an acid and then with an alcohol of formula R²OH optionally in the presence of a water scavenging system, for example concentrated sulphuric acid or an ortho ester e.g. trimethyl orthoformate or triethyl orthoformate or azeotropic distillation, to give a compound of formula XI

XI

in which R² is as initially defined b) reacting the ester of formula XI with a compound of formula XII

XII

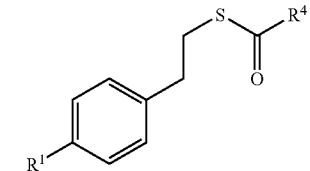

in which R¹ is as initially defined and R⁴ is methyl or phenyl in the presence of a base for example sodium methoxide to give a compound of formula XIII

XIII

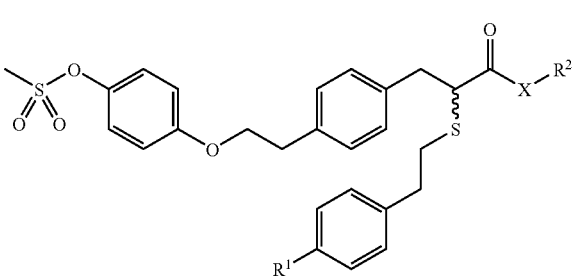

in which R¹, R² and X are as initially defined and c) reacting a compound of formula XIII with an enzyme selected from a) *Mucor miehei* lipase, *Candida rugosa* lipase, *Candida cylindracia* lipase, *Thermomyces lanuginosa* lipase, *Mucor javanicus* lipase and *Rhizopus delemar* lipase when X is O or b) *Pseudomonas cepacia* lipase when X is S in a suitable reaction medium at a temperature in the range of 10-50° C., preferably in the range 20-40° C. to give a compound of formula I

I

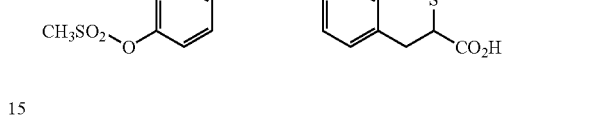

which is enantiomerically enriched and d) optionally reacting the compound of formula I with tert-butylamine in a suitable reaction medium to give the tert-butylammonium salt of the compound of formula I.

In another aspect the present invention provides a telescoped process comprising the steps of a) reacting a compound of formula X

X

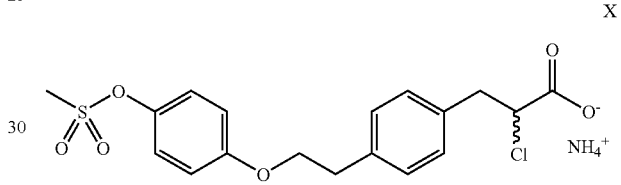

b) reacting a compound of formula X with an acid and then with an alcohol of formula R²OH optionally in the presence of a water scavenging system for example concentrated sulphuric acid or an ortho ester e.g. trimethyl orthoformate or triethyl orthoformate or azeotropic distillation to give a compound of formula XI

XI

in which R² is as initially defined c) reacting the ester of formula XI with a compound of formula XIIa XIIa

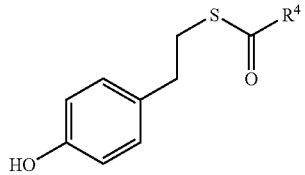

in which R¹ is as initially defined and R⁴ is methyl or phenyl in the presence of a base for example sodium methoxide to give a compound of formula XIIIa

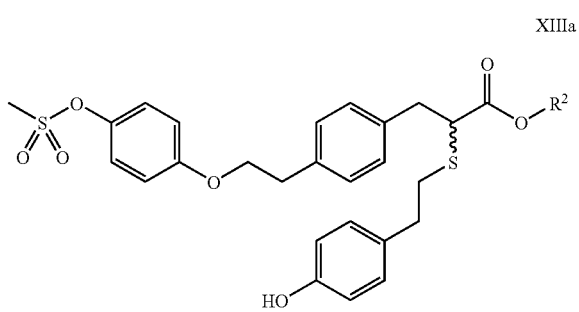

in which R² is as initially defined and d) reacting a compound of formula XIIIa with an enzyme selected from a) *Mucor miehei* lipase, *Candida rugosa* lipase, *Candida cylindracia* lipase, *Thermomyces lanuginosa* lipase, *Mucor javanicus* lipase and *Rhizopus delemar* lipase; to give a compound of formula III

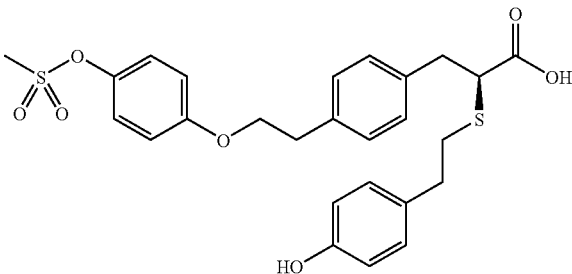

and optionally e) reacting the compound of formula III with tert-butylamine in a suitable reaction medium, for example in the presence of an inert solvent, to give the tert-butylammonium salt of the compound of formula III.

The word telescoped is used to indicate that several process steps are undertaken without isolation of intermediates, thus reducing wastage caused by material transfer. Preferably the telescoped process is carried out as a one-pot process.

In another aspect the present invention provides a process for the preparation of a substantially racemic $C_{1-8}$ alkyl ester of 2-{[2-(4-hydroxyphenyl)ethyl]thio}-3-[4-(2-{4-[(methylsulfonyl)oxy]phenoxy}ethyl)phenyl]propanoic acid which comprises reacting a $C_{1-8}$ alkyl ester 2-{[2-(4-hydroxyphenyl)ethyl]thio}-3-[4-(2-{4-[(methylsulfonyl)oxy]- phenoxy}ethyl)phenyl]propanoic acid enriched in one enantiomer with DBU or tetramethylguanidine or similar base supported on an inert matrix an inert solvent, for example toluene at a temperature in the range of 15-150° C. Optionally the racemic ester may be converted into the corresponding acid by hydrolysis, for example by base hydrolysis or by acid hydrolysis and then optionally the acid reacted with ammonia to give racemic ammonium salt which can then be further reacted in the process to give the desired compound. This racemisation and recycling process improves the efficiency of the process by eliminating wastage of material.

Certain compounds of formula are believed to be novel and are claimed herein as a further aspect of the present invention.

A compound of formula IIa

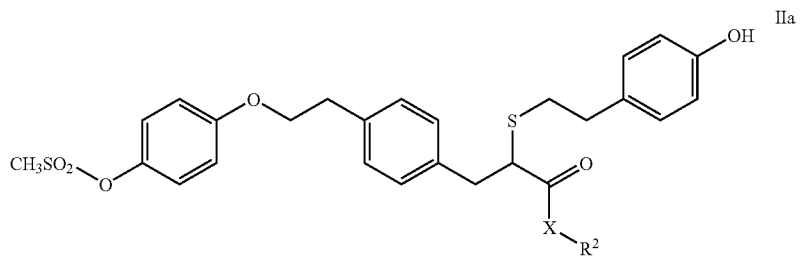

in which i) X is O and R² is ethyl ii) X is O and R² is n-propyl iii) X is O and R² is n-butyl iv) X is S and R² is methyl v) X is S and R² is ethyl vi) X is S and R² is n-propyl or vii) X is S and R² is n-butyl viii) X is S and R² is n-hexyl ix) X is S and R² is n-octyl;

including the (R) and the (S) enantiomer of each compound and all mixtures of the (R) and the (S) enantiomer including the compound in racemic form and when x) X is O and R² is methyl the (S) and the (R) forms.

A compound of formula VIII

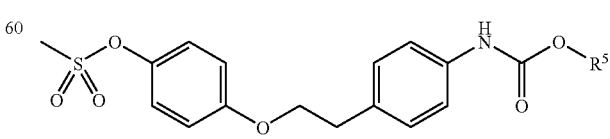

in which R⁵ is as initially defined.

A compound of formula IX which is

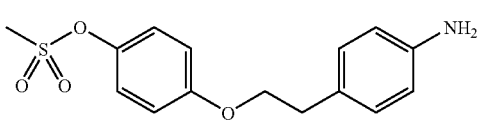

and salts thereof particularly the hydrochloride salt, the hydrobromide salt or the trifluoroacetic acid salt.

A compound of formula X

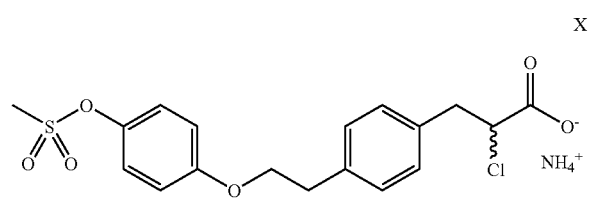

A compound of formula XI

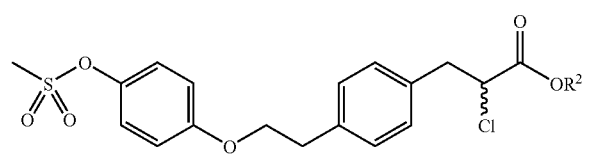

wherein R² is ethyl, n-propyl or n-butyl.

A compound of formula XII

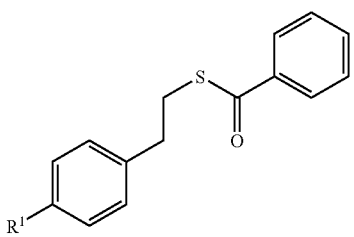

in which R¹ is as initially defined.

A compound of formula XIII

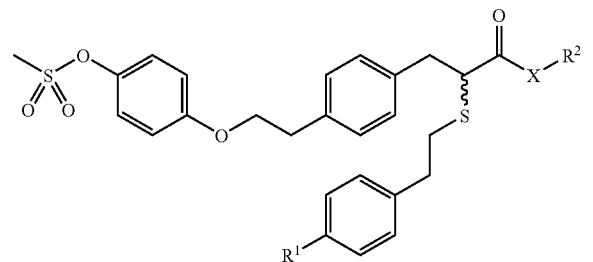

in which R¹, R² and X are as initially defined.

A compound of formula XIV

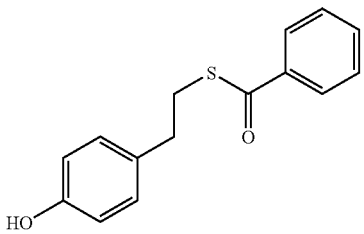

These novel compounds have the advantage of being solid thereby allowing filtration at suitable points during the process which is highly beneficial in removing unwanted impurities during the process. These solids are also easy to handle and move from one vessel to another.

It should be understood that each and every individual step of each of the process schemes listed above are herein claimed as other aspects of the present invention.

The term enantiomerically enriched compound means that there is a preponderance of one enantiomer over the other and that the compound has an optical rotation. For example the compound may contain >60% of one enantiomer for example 70-99.9% particularly 80-99.9% for example 85-99.9%, 90-99.9% or 95-99.9% of one enantiomer. In one embodiment the enantiomer which is predominant is the S enantiomer.

Examples of suitable solvents include $C_{1-6}$alkanols (for example propanol, isopropanol, butanol, tert-butanol, pentanol, amyl alcohol), isoamyl alcohol, ketones (for example acetone and methylisobutyl ketone), ethers (for example for tetrahydrofuran and methyl tert-butyl ether), hydrocarbons (for example toluene), or nitriles (for example acetonitrile or butyronitrile).

EXAMPLES

General Procedures

HPLC Conditions. Reaction mixtures and products were analysed by reverse phase HPLC on a Hewlett Packard 1100 instrument according to the following conditions. Achiral method:—column, Genesis C-18, 100 mm×3.0 mm i.d.; eluent A, 95:5 water:acetonitrile with 0.1% v/v formic acid; eluent B, 95:5 acetonitrile:water with 0.1% v/v formic acid; timetable, (eluent A 100% at 0 mins.; eluent B 100% at 13 mins.; eluent B 100% at 15 mins.; post-run 5 mins.); flow rate 0.75 mL/min.; wavelength 220 nm; injection volume 5 μL; column temperature 35° C.; run time 15 mins. Chiral method:—column, ChiralPak AD-H, 250 mm×4.6 mm i.d.; eluent, methanol with 0.1% v/v formic acid; flow rate 1.0 mL/min.; wavelength 225 nm; injection volume 5 μL; column temperature 45° C.; run time 18 mins. Typical retention times were:—(S)-Acid, 7.8; (S)-Ester, 12.4; (R)-Acid, 13.7; (R)-Ester 15.6 mins.

General Conditions. Melting points were determined using a Griffin melting point apparatus (aluminium heating block) and are uncorrected. ¹H and ¹³C NMR spectra were recorded on a Varian Inova 400 spectrometer at 400 and 100.6 MHz respectively with chemical shifts given in ppm relative to TMS at δ=0. Electrospray (ES⁺) mass spectra were determined on a Micromass Platform LC.

e.e. as used herein means enantiomeric excess and is calculated as follows:

e.e.=[(S)−(R)]/[(S)+(R)]×100 as percent (or R—S for the R-enantiomer);

(S)+(R) always=100. So for example 91% e.e.=95.5% (S)-enantiomer and 4.5% (R)-enantiomer; 93% e.e.=96.5% (S)-enantiomer and 3.5% (R)-enantiomer. Alternatively the chiral purity of (S)-enantiomer may be used which would be 95.5 and 96.5%, respectively in these examples.

Example 1 a) 4-{2-[4-(tert-Butoxycarbonylamino)phenyl]ethoxy]phenyl methanesulfonate

A solution of 4-hydroxyphenyl methanesulfonate (7.04 g @ 82% strength, 30.6 mmol, (prepared by methanesulfonylation of quinol)) dissolved in acetonitrile (72 mL) was added to a mixture of 2-[4-(tert-Butoxycarbonylamino)phenyl] ethyl 4-methylbenzenesulfonate (prepared as described in WO 99/62871) (12.0 g, 30.6 mmol) and potassium carbonate (6.42 g of −325 mesh, 46.0 mmol) under nitrogen and the resulting mixture gently stirred. Acetonitrile (36 mL) and water (12 mL) were added, the stirring rate increased and the reaction mixture was boiled under reflux (80° C.) for 11 to 24 hours. After cooling back to 60° C., the solvent volume was reduced by 6 volumes (~72 mL) by distillation at reduced pressure. Toluene (108 mL) and water (24 mL) were added and the mixture stirred for 5 minutes at 60° C. The solution was filtered through Celite™ (and/or 5% w/w charcoal) and returned to the reaction vessel at 60° C. The phases were allowed to separate and the lower aqueous phase run off and discarded. Dilute aqueous sodium hydroxide solution (10.2 mL of 2.5%, 0.625 M) was added and the mixture stirred at 60° C. for 5 minutes. The phases were allowed to separate and the lower aqueous phase was run off and discarded. Water (24 mL) was added and stirred at 60° C. for 5 minutes, before the phases were allowed to separate and the lower aqueous phase was run off and discarded. The solvent volume was reduced by distillation at atmospheric pressure until a still-head temperature of ~110° C. was achieved. Fresh toluene was added to make the total volume up to 8 volumes (96 mL). The solution was cooled to 60° C., filtered and then cooled to 45° C. Iso-hexane (143 mL) was added dropwise over 1 hour, maintaining the temperature at 45° C., and then the solution cooled to 20° C. at 1° C./minute. The resulting solid was isolated by filtration, washed by displacement with iso-hexane (29 mL) and dried in a vacuum oven at 50° C. to yield the title compound as a buff solid (9.9 g, 79%). HPLC (Rt 10.9 mins); m.p. 117-118° C.; $^1$H NMR (400 MHz, d$_6$-DMSO) δ 9.22 (~1H, s), 7.36 (2H, d, J=8.0 Hz), 7.23 (2H, d, J=8.8 Hz), 7.17 (2H, d, J=8.4 Hz), 6.98 (2H, d, J=9.2 Hz), 4.13 (2H, t, J=6.6 Hz), 3.29 (3H, s), 2.93 (2H, t, J=6.6 Hz), 1.44 (9H, s); $^{13}$C NMR (100.6 MHz, d$_6$-DMSO) δ 157.18, 152.77, 142.44, 137.80, 131.62, 129.04, 124.01, 123.28, 118.15, 115.45, 78.83, 68.69, 36.89, 34.14 and 28.10; MS (ES$^+$) 425 (M+NH$_4^+$, 5%), 308 (10%), 120 (100%).

b) 4-[2-(4-Aminophenyl)ethoxy]phenyl methanesulfonate

Trifluoroacetic acid (7.95 mL, 11.8 g, 102 mmol) was added over 5 minutes to a slurry of 4-{2-[4-(tert-butoxycarbonylamino)phenyl]ethoxy}phenyl methanesulfonate (17.6 g @ 95%, 40.8 mmol) in toluene (176 mL) at 20° C., and then heated to 60° C. to form a dark brown solution. A seed of pure product (0.05% by weight) was added and the reaction mixture heated at 60° C. for 17 hours during which period a dense solid crystallized. The reaction mixture was cooled to 20° C. and the solid isolated by filtration, washed by displacement with toluene (26 mL) and dried in a vacuum oven at 40° C. to yield the title compound as a dense, buff-coloured solid (16.1 g, 94%). HPLC (Rt 6.0 mins); m.p. 131-133° C.; $^1$H NMR (400 MHz, d$_6$-DMSO) δ 7.35 (2H, d, J=8.4 Hz), 7.26 (2H, dt, J=10.8, 3.0 Hz), 7.13 (2H, d, 8.0 Hz), 7.05 (2H, dt, J=10.8, 3.0 Hz), 4.19 (2H, t, J=6.6 Hz), 3.31 (3H, s), 3.02 (2H, t, J=6.6 Hz), 2.9-4.7 (br); $^{13}$C NMR (100.6 MHz, d$_6$-DMSO) δ 157.12, 142.46, 135.56, 133.65, 130.04, 123.31, 121.02, 115.45, 68.43, 36.92 and 34.14; MS (ES$^+$) 308 (M+H$^+$, 100%).

Example 2

Ammonium 2-chloro-3-[4-(2-{4-[(methylsulfonyl)oxy]phenoxy}ethyl)phenyl]-propanoate 4-[2-(4-Aminophenyl)ethoxy]phenyl methanesulfonate (15.9 g, 37.7 mmol) was added to a suitably serviced reaction vessel under nitrogen, followed by copper (I) iodide (0.36 g, 1.9 mmol), acetone (103 mL), and water (2.5 mL) and stirred to form a mobile slurry. Concentrated hydrochloric acid (9.3 mL of 37% w/w, 113 mmol) was added in one portion to form a brown solution, followed by acrylic acid (19.4 mL, 283 mmol) in one portion, and the resulting solution cooled to 3° C. A solution of sodium nitrite (2.95 g, 41.5 mmol) dissolved in water (6.3 mL) was added smoothly to the reaction mixture over at least 10 hours, keeping the reaction temperature at 3° C. Water (1.0 mL) was added as a line wash over at least 1.5 hours, then the reaction mixture stirred at 3° C. for 3 hours before warming to 20° C. over 10 hours. Once all the diazonium chloride had been consumed (<0.1% as determined by HPLC), an aqueous solution of urea (2.0 mL of 20% w/w in water) was added and the reaction mixture stirred for 30 minutes. Ethyl acetate (32 mL), toluene (63 mL), brine (63 mL) and water (32 mL) were added to the reaction mixture, which was stirred for 20 minutes, allowed to settle and the lower green aqueous layer separated and discarded. Brine (63 mL) and water (32 mL) were added to the remaining organic phase. The mixture was stirred for 20 minutes, allowed to settle and the lower colourless aqueous layer separated and discarded. The water/brine washes were repeated. Water (63 mL) was added to the organic phase, stirred for 20 minutes, allowed to settle and the lower colourless aqueous layer separated and discarded. The water wash was repeated four times. Water (127 mL) was added followed by aqueous sodium carbonate (59 mL of a 10% w/w solution in water) carefully in portions, stirred, and the phases allowed to separate (the solution can be heated briefly to 40° C. to improve the separation). The upper organic phase was removed and discarded and the lower aqueous phase returned to the vessel. Ethyl acetate (127 mL) was added followed by concentrated hydrochloric acid (8.8 mL of 37% w/w solution, 107 mmol) in portions to acidify the solution (CO$_2$ may be evolved). After stirring for 20 minutes, the phases were separated and the lower aqueous phase discarded (the solution can be heated briefly to 40° C. to improve the separation). The organic phase was washed with water (63 mL) as described above, and then dried by azeotropic distillation at atmospheric pressure to remove water (106 mL distillate collected on this scale; residual water content of the ethyl acetate solution was 0.5% w/w). The solution was cooled to 20° C. and ammonia in dioxane (85 mL of a 0.5 M solution, 42.7 mmol) added smoothly over 90 minutes at 22° C., during which period a mobile slurry formed. After a minimum of 4 hours at 22° C., the reaction mixture was cooled to 0° C. for 75 minutes, and the solid isolated by filtration under a nitrogen pad. The product was washed by displacement with chilled (0° C.) ethyl acetate (30 mL) and dried in a vacuum oven at 40° C. to yield the title compound as a buff-coloured solid (9.2 g corrected for strength, 58.9%). HPLC (Rt 9.5 mins); m.p. 148-150° C.; $^1$H NMR (400 MHz, d$_6$-DMSO) δ 6.9-7.8 (~3H, vbs), 7.25 (2H, d, J=9.2 Hz), 7.22 (2H, d, J=8.4 Hz), 7.17 (2H, d, J=8.0 Hz), 7.02 (2H, d, J=9.2 Hz), 4.16-4.22 (3H, m), 3.31 (3H, s), 3.26 (1H, dd, J=14.0, 5.6 Hz), 3.00 (2H, t, J=7.0 Hz), 2.88 (1H, dd, J=14.0, 8.8 Hz); $^{13}$C NMR (100.6 MHz, d$_6$-DMSO) δ 170.54, 157.15, 142.45, 136.66, 135.89, 129.20, 128.58, 123.28, 115.48, 68.56, 63.91, 41.37, 36.89 and 34.44; MS (ES$^+$) 416 (M+NH$_4^+$, 60%).

Example 2b

2-Chloro-3-[4-(2-{4-[(methylsulfonyl)oxy]phenoxy}ethyl)phenyl]propanoic acid

Alternatively the free acid could be isolated as follows. The ethyl acetate extract from example 2a was dried over MgSO$_4$ and concentrated to an oil. This was either dissolved in hot toluene (64 mL) and ethyl acetate (32 mL), the ethyl acetate distilled off and the solution cooled; or dissolved in toluene at reflux (32 mL), cooled to 22° C. and iso-hexane (32 mL) added; or crystallised from hot anisole (159 mL); to yield in each case the title compound as an off-white solid. HPLC (Rt 9.5 mins); m.p. 88-89° C.; $^1$H NMR (400 MHz, d$_6$-DMSO) δ 7.21-7.28 (6H, m), 7.01 (2H, d, J=8.8 Hz), 4.67 (1H, t, J=7.4 Hz), 4.19 (2H, t, J=7.0 Hz), 3.31 (3H, s), 3.27 (1H, dd, J=14.0, 6.8 Hz), 3.05 (1H, dd, J=14.0, 8.0 Hz), 3.01 (2H, t, J=6.6 Hz); $^{13}$C NMR (100.6 MHz, d$_6$-DMSO) δ 170.05, 157.15, 142.45, 136.79, 134.38, 129.31, 128.87, 123.31, 115.48, 68.48, 58.09, between 39.08 and 40.11 (under DMSO signal), 36.92 and 34.44.

Example 3

2-(4-Hydroxyphenyl)ethyl thiobenzoate

Thionyl chloride (5.5 mL, 75.5 mmol) was added smoothly over 1 hour to a clear solution of 4-hydroxyphenylethanol (10.0 g, 70.9 mmol) and triethylamine (10.5 mL, 74.5 mmol) dissolved in toluene (37.2 mL) and acetonitrile (10.0 mL) at or below 60° C., followed by a line wash of toluene (1.4 mL). A light yellow to light brown coloured solution resulted which was held at 60° C. for 2 hours, during which time some SO$_2$ was evolved. A saturated solution of sodium bicarbonate (20 mL) was added carefully at 60° C., stirred for 15 minutes, allowed to settle and the lower aqueous phase removed and discarded. The bicarbonate wash was repeated, followed by a water wash (20 mL). The organic phase was heated to toluene reflux under Dean and Stark conditions to a constant head temperature to remove residual dissolved gases and water. The total distillate was measured and fresh toluene added to replace it (30 mL on this scale). The reaction mixture was cooled back to 80° C. and thiobenzoic acid (10.5 g, 74.5 mmol) added slowly from a warmed measure vessel (alternatively, the thiobenzoic acid can be dissolved in the fresh toluene required to make up the volume). Triethylamine (10.5 mL, 74.5 mmol) was added smoothly over 30 minutes, followed by a toluene line wash (11.4 mL), and the reaction mixture stirred at 80° C. for 8 hours. Dilute aqueous hydrochloric acid (20 mL of 0.5 M) was added, stirred vigorously for 15 minutes, allowed to settle and the lower aqueous phase removed and discarded. The procedure was repeated with water (20 mL). The organic phase was cooled to 60° C. and given a second water wash. Iso-hexane (65 mL) was added to the toluene phase over 1 hour, and the resulting solution cooled smoothly to 0° C. over 4 hours with good stirring. The product crystallized at ~33° C. The resulting slurry was chilled at 0° C. for at least 1 hour before being isolated by filtration and washed by displacement with the recycled mother liquors (as a vessel rinse) and then with fresh iso-hexane (20 mL), to yield the title compound as a light buff-coloured solid (14.7 g, 77%). HPLC (Rt 10.1 min); m.p. 90-91° C.; $^1$H NMR (400 MHz, CDCl$_3$) δ 7.96 (2H, d, J=7.2 Hz), 7.57 (1H, t, J=7.4 Hz), 7.44 (2H, t, J=7.8 Hz), 7.13 (2H, d, J=8.8 Hz), 6.79 (2H, d, J=8.4 Hz), 5.0 (1H, bs), 3.28 (2H, t, J=7.6 Hz), 2.90 (2H, t, J=7.8 Hz); $^{13}$C NMR (100.6 MHz, CDCl$_3$) δ 192.26, 154.23, 137.09, 133.51, 132.23, 129.78, 128.59, 127.19, 115.35, 34.99, 30.71; MS (ES$^+$) 259 (M+H$^+$, 100%), 182 ((M+H-Ph)$^+$, 60%).

Example 4

Methyl 2-{[2-(4-hydroxyphenyl)ethyl]thio}-3-[4-(2-{4-[(methylsulfonyl)oxy]-phenoxy}ethyl)phenyl]propanoate Concentrated sulfuric acid (2.2 mL, 60.0 mmol) was added smoothly over 30 minutes to a slurry of ammonium 2-chloro-3-[4-(2-{4-[(methylsulfonyl)oxy]phenoxy}ethyl)phenyl]-propanoate (15.0 g @ 91.4% strength, 33.0 mmol) in methanol (60 mL) and trimethyl orthoformate (10.9 mL, 39.6 mmol), followed by a line wash of methanol (7.5 mL). The reaction mixture was heated to 60° C. for 2 hours to form a dark solution, and then cooled back to 50° C. 2-(4-Hydroxyphenyl)ethyl thiobenzoate (10.4 g @ 97.9%, 39.6 mmol) was added in one portion and the reaction vessel purged with nitrogen. Sodium methoxide (19.0 mL of 25% strength solution in methanol, 82.4 mmol) was added smoothly over 30 minutes followed by a methanol line wash (7.5 mL), and the reaction stirred at 50° C. for 5 hours, during which time a slightly cloudy precipitate formed. The reaction mixture was cooled to 35° C., water (98 mL) was added with vigorous stirring, followed by methyl tert-butyl ether (MTBE) (98 mL), the mixture was stirred for 15 minutes, allowed to settle, and the lower aqueous phase removed and discarded. The remaining MTBE phase was washed with dilute aqueous hydrochloric acid solution (0.03 mL of 32% w/w in 49 mL of water), and then with water (49 mL), both at 35° C. The amount of the product ester in the MTBE solution was assayed by LC and used without further purification in the next stage. HPLC (Rt 10.9 min); m.p. oil; $^1$H NMR (400 MHz, d$_6$-DMSO) δ 9.20 (1H, s), 7.15-7.24 (6H, m), 7.00 (2H, d, J=8.8 Hz), 6.97 (2H, d, J=8.4 Hz), 6.66 (2H, d, J=8.4 Hz), 4.18 (2H, t, J=7.0 Hz), 3.66 (1H, dd, J=9.2, 6.4 Hz), 3.58 (3H, s), 3.31 (3H, s), 3.05 (1H, dd, J=14.0, 8.8 Hz) 3.00 (2H, t, J=6.8 Hz), 2.85 (1H, dd, J=14.0, 6.8 Hz), 2.77 (2H, t, J=7.2 Hz), 2.61-2.71 (2H, m); $^{13}$C NMR (100.6 MHz, d$_6$-DMSO) δ 172.07, 157.14, 155.71, 142.45, 136.37, 135.93, 130.19, 129.35, 128.89, 128.81, 123.29, 115.47, 115.02, 68.48, 51.87, 46.99, 36.90, 36.79, 34.40, 34.35 and 32.68; MS (ES$^+$) 548 (M+NH$_4^+$, 70%), 531 (M+H$^+$, 90%), 471 (M-CO$_2$Me$^+$, 100%).

Example 5

(S)-(−)-2-{[2-(4-Hydroxyphenyl)ethyl]thio}-3-[4-(2-{4-[(methylsulfonyl)oxy]phenoxy}-ethyl)phenyl]propanoic acid A solution of methyl 2-{[2-(4-hydroxyphenyl)ethyl]thio}-3-[4-(2-{4-[(methylsulfonyl)oxy]phenoxy}ethyl)phenyl]

propanoate (93 mL of a 0.17 mg/mL solution in MTBE, 15.8 g, 29.8 mmol) was reduced in volume by distillation to ~3 volumes (47 mL in this case). A solution of tert-butanol/water (95 mL of a 9:1 solution, 6 volumes) was added and the distillation was continued to remove a further 4 volumes of distillate (~63 mL in this case), before cooling to 25° C. A further 1 volume of tert-butanol/water (16 mL of a 9:1 solution) was added, followed by Lipozyme RM IM (1.6 g of immobilized enzyme, 10% w/w with respect to starting ester). The reaction mixture was heated to 35° C. and stirred gently for more than 16 hours until ~30-35% conversion had occurred. The enzyme was removed by filtration and the solid washed with tert-butanol/water (16 mL of a 9:1 solution). The amount of (S)-acid product in the tert-butanol/water solution was assayed by LC and used without further purification in the next stage (5.3 g by HPLC assay, 35% based on starting ester). HPLC (Rt 9.8 min); chiral HPLC (typically 91-93% e.e. in solution).

Example 6 tert-Butylammonium (S)-(−)-2-{[2-(4-hydroxyphenyl)ethyl]thio}-3-[4-(2-{4-[(methylsulfonyl)oxy]phenoxy}ethyl)phenyl]propanoate A solution of (S)-(−)-2-{[2-(4-Hydroxyphenyl)ethyl]thio}-3-[4-(2-{4-[(methylsulfonyl)oxy]phenoxy}ethyl)phenyl]propanoic acid (100 mL of a 0.053 g/mL solution in 9:1 tert-butanol/water, 5.3 g, 10.3 mmol) was reduced in volume by atmospheric distillation to half volume (50 mL in this case). Toluene (100 mL) was added and distillation continued until a still-head temperature of 109° C. achieved (a further 80 mL of distillate was collected in this case). The solution was cooled to 60° C. and fresh toluene (80 mL) and water (50 mL) added, followed by a solution of sodium carbonate (18 mL of a 10% w/w solution in water). The solution was stirred at 60° C. for 10 minutes, allowed to settle and the lower aqueous layer removed and retained; the upper organic phase containing (R)-methyl 2-{[2-(4-hydroxyphenyl)ethyl]thio}-3-[4-(2-{4-[(methylsulfonyl)oxy]phenoxy}ethyl)phenyl]propanoate was removed. The aqueous phase was returned to the vessel followed by butyronitrile (20 mL) and stirred vigorously for 20 minutes. The phases were allowed to separate and the highly-coloured upper organic phase removed and discarded. Butyronitrile (100 mL) was added, followed by aqueous hydrochloric acid (35 mL of 1.0 M solution) smoothly over 10 minutes with good stirring at 50° C., before being allowed to settle and the lower aqueous phase removed and discarded. Water (25 mL) was added at 50° C., stirred vigorously for 5 minutes, allowed to settle and the lower aqueous phase removed and discarded. The butyronitrile solution was then dried by azeotropic distillation at atmospheric pressure to remove water (5.5 mL collected on this scale; residual water content of the butyronitrile solution was measured at 0.1%), before cooling to 20° C. tert-Butylamine (0.83 g, 1.19 mL, 11.3 mmol) was added, the solution warmed to 45° C., and a seed (6 mg, 0.1% w/w) added. The solution was stirred at 45° C. for 86 hours, and then cooled smoothly to 20° C. at 0.1° C./hour, during which time a solid crystallised. The solid was isolated by filtration, washed sequentially by displacement with butyronitrile (10.6 mL) and MTBE (10.6 mL), and dried in a vacuum oven at 50° C. to yield the title compound as a white solid (4.7 g, 88% based on starting (S)-Acid). HPLC (Rt 9.8 min); chiral HPLC (typically 95% e.e.); m.p. 132-134° C.; $^1$H NMR (400 MHz, $d_6$-DMSO) δ 7.19 (2H, d, J=8.8 Hz), 7.21 (2H, d, J=9.2 Hz), 7.10 (2H, d, J=9.2 Hz), 6.95 (2H, d, J=8.8 Hz), 6.88 (2H, d, J=8.0 Hz), 6.59 (2H, d, J=8.4 Hz), 4.10 (2H, t, J=6.8 Hz), 3.25 (3H, s), 3.20 (1H, dd, J=8.4, 6.0 Hz), 3.02 (1H, dd, J=13.6, 8.8 Hz), 2.92 (2H, t, J=6.8 Hz), 2.44-2.72 (5H, m), 1.13 (9H, s); $^{13}$C NMR (100.6 MHz, $d_6$-DMSO) δ 173.86, 157.15, 155.71, 142.44, 138.39, 135.39, 130.84, 129.18, 128.95, 128.45, 123.27, 115.45, 114.96, 68.63, 51.21, 49.93, 36.88, 34.80, 34.45, 32.65, 27.65; MS (ES$^+$) 534 (M+NH$_4^+$, 40%), 517 (M+H$^+$, 27%), 471 (M-CO$_2$H$^+$, 100%).

Example 7 tert-Butylammonium (S)-(−)-2-{[2-(4-hydroxyphenyl)ethyl]thio}-3-[4-(2-{4-[(methylsulfonyl)oxy]phenoxy}ethyl)phenyl]propanoate Concentrated sulfuric acid (2.2 mL, 60.0 mmol) was added smoothly over 30 minutes to a slurry of ammonium 2-chloro-3-[4-(2-{4-[(methylsulfonyl)oxy]phenoxy}ethyl)phenyl]-propanoate (15.0 g @ 91.4% strength, 33.0 mmol) in methanol (60 mL) and trimethyl orthoformate (10.9 mL, 39.6 mmol), followed by a line wash of methanol (7.5 mL). The reaction mixture was heated to 60° C. for 2 hours to form a dark solution, and then cooled back to 50° C. 2-(4-Hydroxyphenyl)ethyl thiobenzoate (10.4 g @ 97.9%, 39.6 mmol) was added in one portion and the reaction vessel thoroughly purged with nitrogen. Sodium methoxide (19.0 mL of 25% strength solution in methanol, 82.4 mmol) was added smoothly over 30 minutes followed by a methanol line wash (7.5 mL), and the reaction stirred at 50° C. for 5 hours, during which time a slightly cloudy precipitate formed. The reaction mixture was cooled to 35° C., water (98 mL) was added with vigorous stirring, followed by MTBE (98 mL), the mixture stirred for 15 minutes, allowed to settle, and the lower aqueous phase removed and discarded. The remaining MTBE phase was washed with dilute aqueous hydrochloric acid solution (0.03 mL of 32% w/w in 49 mL of water), and then with water (49 mL), both at 35° C. The MTBE solution was reduced in volume by distillation to ~3 volumes (47 mL in this case). A solution of tert-butanol/water (95 mL of a 9:1 solution, 6 volumes) was added and the distillation was continued to remove a further 4 volumes of distillate (~63 mL in this case), before cooling to 25° C. A further 1 volume of tert-butanol/water (16 mL of a 9:1 solution) was added, followed by Lipozyme RM IM (1.6 g of immobilized enzyme, 10% w/w with starting ester). The reaction mixture was heated to 35° C. and stirred gently for more than 16 hours until ~30-35% conversion had occurred. The enzyme was removed by filtration and the solid washed with tert-butanol/water (16 mL of a 9:1 solution). Chiral HPLC of the product (S)-Acid solution was typically 91-93% e.e. The product (S)-Acid solution was reduced in volume by atmospheric distillation to half volume (50 mL in this case). Toluene (100 mL) was added and distillation continued until a still-head temperature of 109° C. achieved (a further 80 mL of distillate was collected in this case). The solution was cooled to 60° C. and fresh toluene (80 mL) and water (50 mL) added, followed by a solution of sodium carbonate (18 mL of a 10% w/w solution in water). The solution was stirred at 60° C. for 10 minutes, allowed to settle and the lower aqueous layer removed and retained; the upper organic phase containing (R)-Ester was removed. The aqueous phase was returned to the vessel followed by butyronitrile (20 mL) and stirred vigorously for 20 minutes. The phases were allowed to separate and the highly-coloured upper organic phase removed and discarded. Butyronitrile (100 mL) was added, followed by aqueous hydrochloric acid (35 mL of 1.0M solution) smoothly over 10 minutes with good stirring at 50° C., before being allowed to settle and the lower aqueous phase removed and discarded. Water (25 mL) was added at 50° C., stirred vigorously for 5 minutes, allowed to settle and the lower aqueous phase removed and discarded. The butyronitrile solution was then dried by azeotropic distillation at atmospheric pressure to remove water (5.5 mL collected on this scale; residual water content of the butyronitrile solution was measured at 0.1%), before cooling to 20° C. tert-Butylamine (0.83 g, 1.19 mL, 11.3 mmol) was added, the solution warmed to 45° C., and product seed (6 mg, 0.1% w/w) added. The solution was stirred at 45° C. for 86 hours, and then cooled smoothly to 20° C. at 0.1° C./hour, during which time a solid crystallised. The solid was isolated by filtration, washed sequentially by displacement with butyronitrile (10.6 mL) and MTBE (10.6 mL), and dried in a vacuum oven at 50° C. to yield the title compound as a white solid (4.7 g, 24% based on starting salt). HPLC (Rt 9.8 min); chiral HPLC (typically 95% e.e.); m.p. 132-134° C.; $^1$H NMR (400 MHz, d$_6$-DMSO) δ 7.19 (2H, d, J=8.8 Hz), 7.21 (2H, d, J=9.2 Hz), 7.10 (2H, d, J=9.2 Hz), 6.95 (2H, d, J=8.8 Hz), 6.88 (2H, d, J=8.0 Hz), 6.59 (2H, d, J=8.4 Hz), 4.10 (2H, t, J=6.8 Hz), 3.25 (3H, s), 3.20 (1H, dd, J=8.4, 6.0 Hz), 3.02 (1H, dd, J=13.6, 8.8 Hz), 2.92 (2H, t, J=6.8 Hz), 2.44-2.72 (5H, m), 1.13 (9H, s); $^{13}$C NMR (100.6 MHz, d$_6$-DMSO) δ 173.86, 157.15, 155.71, 142.44, 138.39, 135.39, 130.84, 129.18, 128.95, 128.45, 123.27, 115.45, 114.96, 68.63, 51.21, 49.93, 36.88, 34.80, 34.45, 32.65, 27.65; MS (ES$^+$) 534 (M+NH$_4^+$, 40%), 517 (M+H$^+$, 27%), 471 (M-CO$_2$H$^+$, 100%).

Example 8 tert-Butylammonium (S)-(−)-2-{[2-(4-hydroxyphenyl)ethyl]thio}-3-[4-(2-{4-[(methylsulfonyl)oxy]phenoxy}ethyl)phenyl]propanoate Crude tert-Butylammonium 2-{[2-(4-hydroxyphenyl)ethyl]thio}-3-[4-(2-{4-[(methylsulfonyl)oxy]phenoxy}ethyl)phenyl]propanoate (11.7 g, 19.8 mmol) was stirred in warm absolute ethanol (53.8 mL) at 71° C. to achieve complete dissolution. The resulting solution was screened into a second vessel through a 1 μm filter, followed by a line wash of warm ethanol (4.7 mL), and the solution allowed to cool to 60° C. Seed crystals (60 mg, 0.5% w/w) were added as a slurry in ethanol (0.5 mL) and the solution held at 60° C. for 30 minutes before cooling to 51° C. at 0.1° C./minute. The solution was held at 51° C. for 3 hours, during which period further seed crystals formed. The slurry was cooled to 46° C. at 0.1° C./minute, and held for 3 hours; then to 41° C. at 0.1° C./minute, and held for 3 hours; then to 31° C. at 0.1° C./minute, and held for 2 hours; then to 17° C. at 0.17° C./minute, and held for at least 5-6 hours. The solid was isolated by filtration, washed by displacement with absolute ethanol (11.7 mL) and dried in a vacuum oven at 50° C. to yield the title compound as a white solid (10.2 g, 87%). HPLC (Rt 9.8 min); chiral HPLC (typically 98% e.e.); mp 137-139° C.; MS (ES$^+$) 534 (M+NH$_4^+$, 20%), 517 (M+H$^+$, 30%), 471 (M-CO$_2$H$^+$, 100%). Other data as noted for the Crude stage above.

Example 9

Racemisation/Recycle Process to give (S)-2-{[2-(4-Hydroxyphenyl)ethyl]thio}-3-[4-(2-{4-[(methylsulfonyl)oxy]phenoxy}ethyl)phenyl]propanoic acid and its tert-butylammonium salt (R)-Methyl 2-{[2-(4-hydroxyphenyl)ethyl]thio}-3-[4-(2-{4-[(methylsulfonyl)oxy]-phenoxy}ethyl)phenyl]propanoate was recycled by a racemisation, hydrolysis and salt crystallization process to provide further 2-{[2-(4-hydroxyphenyl)ethyl]thio}-3-[4-(2-{4-[(methylsulfonyl)oxy]phenoxy}ethyl)phenyl]propanoic acid as follows: 1,8 diazabicyclo[5.4.0]undec-7-ene (DBU) (1.5 mL, 10.2 mmol) was added to a solution of (R)-Methyl 2-{[2-(4-hydroxyphenyl)ethyl]thio}-3-[4-(2-{4-[(methylsulfonyl)oxy]-phenoxy}ethyl)phenyl]propanoate (10.8 g, 20.4 mmol) in toluene (200 mL) and stirred at 50° C. for 17 hours. Chiral HPLC assay was 0% (±2) after this period. Water (22 mL) was added and the solution cooled to 40° C. Aqueous sodium hydroxide solution (2.9 mL of 32% w/w, 30.5 mmol) was added and the solution stirred at 40° C. for 2 hours. A second charge of sodium hydroxide solution (1.0 mL, 10.2 mmol) was added and the solution stirred at 40° C. for 1 hour. A third charge of sodium hydroxide solution (1.0 mL, 10.2 mmol) was added and the solution stirred at 40° C. for 17 hours, before cooling to 20° C. The lower aqueous phase was separated and retained; the upper toluene phase was discarded. MTBE (108 mL) was added to the aqueous phase followed by an aqueous sulfuric acid solution (40 mL of 10% w/w, 40.7 mmol) with stirring for 10 minutes. The lower aqueous phase was separated and discarded; the upper organic phase was washed with water (39 mL), separated and then dried by azeotropic distillation at atmospheric pressure to remove residual water (2.4 mL collected on this scale). Methanol (19 mL), trimethylorthoformate (6.7 mL, 61.1 mmol) and concentrated sulfuric acid (0.45 mL, 0.4 mmol) were added sequentially to the dried MTBE solution and then heated at reflux for 17 hours before cooling to 25° C. Water (22 mL) and aqueous sodium carbonate solution (21 mL of 10% w/w, 20.4 mmol) were added, stirred for 5 minutes, and the lower aqueous phase separated and discarded. Water (39 mL) was added to the organic phase, stirred for 5 minutes, allowed to settle and the lower aqueous phase separated and discarded. This water wash was repeated. The MTBE solution of racemic methyl 2-{[2-(4-hydroxyphenyl)ethyl]thio}-3-[4-(2-{4-[(methylsulfonyl)oxy]phenoxy}ethyl)phenyl]-propanoate was reduced in volume by distillation to ~5 volumes (i.e. 54 mL; 54 mL distillate was collected in this case). A solution of tert-butanol/water (66 mL of a 9:1 solution, 6.1 volumes) was added and the distillation was continued to remove a further 4 volumes of distillate (~45 mL in this case), before cooling to 20° C. A further 1 volume of tert-butanol/water (11 mL of a 9:1 solution) was added, followed by Lipozyme RM IM (1.08 g of immobilized enzyme, 10% w/w with respect to Racemic Ester). The reaction mixture was heated to 35° C. and stirred gently for more than 16 hours until ~30-35% conversion had occurred. The enzyme was removed by filtration and the solid washed with tert-butanol/water (5 mL of a 9:1 solution). The amount of (S)-2-{[2-(4-hydroxyphenyl)ethyl]thio}-3-[4-(2-{4-[(methylsulfonyl)oxy]phenoxy}ethyl)phenyl]-propanoic acid ((S)-Acid) in the tert-butanol/water solution was assayed by LC and used without further purification in the next stage (2.8 g of (S)-Acid by LC assay in 49 mL of solution). This acid was converted into tert-butylammonium (S)-(−)-2-{[2-(4-hydroxy-phenyl)ethyl]thio}-3-[4-(2-{4-[(methylsulfonyl)oxy]phenoxy}ethyl)phenyl]propanoate as described in Example 6.

Yield (21% 2.5 g on this scale). Chiral HPLC (typically 95% e.e.).

Example 10 tert-Butylammonium 2-{[2-(4-hydroxyphenyl)ethyl]thio}-3-[4-(2-{4-[(methylsulfonyl)oxy]phenoxy}ethyl)phenyl]propanoate (racemic)

Ammonium 2-chloro-3-[4-(2-{4-[(methylsulfonyl)oxy]phenoxy}ethyl)phenyl]propanoate (90%, 1.55 g, 25.0 mmol)

and 2-(4-hydroxyphenyl)ethyl thiobenzoate (98%, 8.57 g, 32.5 mmol, 1.3 eq) were charged to a reaction vessel under nitrogen. Tetrahydrofuran (THF) (60 mL, 5 vol) was added and the mixture was warmed to 30° C. To the resulting suspension was added a solution of sodium methoxide (25% wt/vol in methanol) (17 mL, 74 mmol, 3 eq.) at a rate of 0.25 mL/min. The resulting grey suspension was heated to 40° C. for 2 hours and allowed to stand at ambient temperature overnight without stirring. The mixture was re-heated to 40° C. and the progress of the reaction was monitored by HPLC. After 4 hours, 97% conversion was achieved and the mixture was quenched by the addition of toluene (50 mL, 5 vol) and water (10 mL, 1 vol) and the mixture was vigorously stirred until all two clear phases were obtained. The pH of the lower aqueous phase was adjusted from ~12 to ~10.0 by addition of hydrochloric acid (~4 mL @ 6 N) and the mixture was allowed to settle. The lower aqueous phase was separated and retained; the toluene phase was re-extracted with water (10 mL). The combined aqueous phases were washed with toluene (twice, 10 mL) (this gave three phases when allowed to settle: a lower oily phase containing product, clear aqueous middle phase, upper toluene phase). The lower phase was collected, the middle and upper phase were discarded, and this was allowed to stand overnight (no degradation observed as judged by HPLC). The aqueous phase was acidified to pH ~1.0 by addition of 6 N hydrochloric acid and the product was extracted into butyronitrile (2×30 mL, 1×20 mL). The butyronitrile solution was dried by azeotropic distillation under reduced pressure (45° C., 60 mbar). The resulting clear brown solution (75 mL, 7.5 vol) was held at 45° C. and tert-butylamine (2.9 mL, 27.5 mmol, 1.1 eq.) was added, before seeding with an authentic sample of title material (100 mg). As the resulting suspension thickened iso-butyl acetate (40 mL) was charged and the mixture was allowed to settle overnight. After filtration, the cake was washed with iso-butyl acetate (2×10 mL), 1:1 iso-hexane/iso-butyl acetate (20 mL) and iso-hexane (25 mL). The product was dried in vacuo at 40° C. to give the title compound as an off-white solid (13.41 g, 91%). HPLC (Rt 9.8 min); m.p. 125-129° C. Other physical and spectral data were consistent with those reported above.

Example 11

S-Ethyl 2-{[2-(4-hydroxyphenyl)ethyl]thio}-3-[4-(2-{4-[(methylsulfonyl)oxy]phenoxy}-ethyl)phenyl]propanethioate A solution of racemic 2-{[2-(4-hydroxyphenyl)thio}-3-[4-(2-{4-[(methylsulfonyl)oxy]phenoxy}ethyl)phenyl]propanoic acid (45 g @ 80% strength, containing 8% wt/wt benzoic acid, 70 mmol) in ethyl acetate (225 mL, 5 vol) was cooled to 0-5° C. Solid chloromethylene-dimethylammonium chloride (Vilsmeier reagent @ 95% strength, 20.6 g, 161 mmol, 2.3 eq) was added in 4 equal portions over 1.5 hours maintaining a temperature of 0-5° C. The resulting turbid mixture was stirred at the same temperature for 2.5 hours and was subsequently added dropwise to an ice-cold vigorously stirred solution of ethanethiol (7.8 mL, 105 mmol, 1.5 eq.) in aqueous phosphate buffer (pH 7,200 mL). The pH was constantly monitored and kept between 6 and 7.5 by simultaneous addition of 32% NaOH solution. After 30 minutes at low temperature, the batch was allowed to warm to ambient temperature overnight. The organic phase was separated, dried (MgSO$_4$) and concentrated in vacuo to give the crude product as brown oil (43.82 g, 114%). The crude compound was purified by flash chromatography (20:80 to 50:50 EtOAc:iso-hexane; silica) to yield the title compound as a pale yellow oil (31.5 g, 81%). HPLC (Rt 11.6 min); m.p. oil; $^1$H NMR (400 MHz, d$_6$-DMSO) δ 9.19 (1H, s), 7.18-7.28 (4H, m), 7.14 (2H, d, J=8.1 Hz), 7.00-6.94 (4H, m), 6.65 (2H, d, J=8.4 Hz), 4.15 (2H, t, J=6.8 Hz), 3.87-3.83 (1H, m), 3.29 (3H, s), 3.08 (1H, dd, J=14.0, 8.4 Hz) 2.98 (2H, t, J=6.8 Hz), 2.87 (1H, dd, J=14.0, 7.0 Hz), 2.80-2.67 (4H, m), 2.66-2.60 (2H, m), 1.08 (3H, t, J=7.2 Hz); $^{13}$C NMR (100.6 MHz, d$_6$-DMSO) δ 198.14, 157.15, 155.73, 142.45, 136.37, 135.52, 130.14, 129.34, 129.22, 129.07, 123.28, 115.39, 115.04, 68.51, 55.29, 37.14, 36.88, 34.41, 34.34, 32.78, 22.98 and 14.53.

The following analogous thiol esters of were prepared using the method described above or slight modifications:

| | HPLC rt/min |
|---|---|
| S-Methyl 2-{[2-(4-hydroxyphenyl)ethyl]thio}-3-[4-(2-{4-[(methylsulfonyl)oxy]phenoxy}ethyl)phenyl]propanethioate | 11.2 |
| S-Ethyl 2-{[2-(4-hydroxyphenyl)ethyl]thio}-3-[4-(2-{4-[(methylsulfonyl)oxy]phenoxy}ethyl)phenyl]propanethioate | 12.5 |
| S-n-butyl 2-{[2-(4-hydroxyphenyl)ethyl]thio}-3-[4-(2-{4-[(methylsulfonyl)oxy]phenoxy}ethyl)phenyl]propanethioate | 13.2 S 14.1 R |
| S-Octyl 2-{[2-(4-hydroxyphenyl)ethyl]thio}-3-[4-(2-{4-[(methylsulfonyl)oxy]phenoxy}ethyl)phenyl]propanethioate | 14.1 |

Example 12

Resolution of Methyl 2-{[2-(4-hydroxyphenyl)ethyl]thio}-3-[4-(2-{4-[(methylsulfonyl)oxy]phenoxy}ethyl)phenyl]propanoate Racemic methyl 2-{[2-(4-hydroxyphenyl)ethyl]thio}-3-[4-(2-{4-[(methylsulfonyl)oxy]-phenoxy}ethyl)phenyl]propanoate (0.4 g) was dissolved in 9:1 t-BuOH-water (70 mL). This stock solution was divided into 1 mL aliquots for screening reactions. 5-10 mg biocatalyst was added and the reactions warmed in an orbital shaker thermostatted at 40° C. and 300 rpm. The course of the reaction was followed by reverse phase HPLC and experiments which showed acceptable conversion were further analysed by chiral HPLC. Biocatalysts which showed promising conversion are listed below. All enzymes which catalysed hydrolysis were (S)-selective.

| Biocatalyst | Conversion @ 40 hours (%) | e.e. (S)-Acid product (%) |
|---|---|---|
| *Mucor javanicus* lipase | 20 | 100 |
| *Rhizopus delmar* lipase | 45 | 90 |
| *Candia rugosa* lipase Lipase OF Metio | 48 | 95 |
| *Mucor miehei* lipase (Lipozyme RM) | 48 | 80 |
| *Mucor miehei* lipase (Roche L-9 C-2) | 40 | 95 |
| *Thermomyces lanuginosa* lipase (Roche L-8) | 30 | 95 |
| *Candida cylindracia* lipase | 40 | 95 |
| *Candia rugosa* lipase (Amano AYS) | 20 | 100 |

(S)-Acid = (S)-2-{[2-(4-hydroxyphenyl)ethyl]thio}-3-[4-(2-{4-[(methylsulfonyl)oxy]-phenoxy}ethyl)phenyl]propanoic acid Example 13

Transesterification of Methyl 2-{[2-(4-hydroxyphenyl)ethyl]thio}-3-[4-(2-{4-[(methylsulfonyl)oxy]phenoxy}ethyl)phenyl]propanoate Racemic methyl 2-{[2-(4-hydroxyphenyl)ethyl]thio}-3-[4-(2-{4-[(methylsulfonyl)oxy]-phenoxy}ethyl)phenyl]propanoate (0.1 g) was dissolved in 1:1 t-butylmethyl ether (TBME)-n-BuOH (with 3% v/v water). To this solution was added *Mucor miehei* lipase catalyst (Roche L9 C-2; 5 mg), and the mixture warmed to 40° C. After 2 days, HPLC showed 45% conversion to n-butyl(S)-2-{[2-(4-hydroxyphenyl)ethyl]thio}-3-[4-(2-{4-[(methylsulfonyl)oxy]phenoxy}ethyl)phenyl]propanoate.

Example 14

Hydrolysis of Racemic Thioesters of 2-{[2-(4-hydroxyphenyl)ethyl]thio}-3-[4-(2-{4-[(methylsulfonyl)oxy]phenoxy}ethyl)phenyl]propanoate A solution of racemic S-Ethyl 2-{[2-(4-hydroxyphenyl)ethyl]thio}-3-[4-(2-{4-[(methylsulfonyl)oxy]phenoxy}ethyl)phenyl]propanethioate was prepared in 9:1 t-BuOH-water at a concentration of ~20 mg/ml. This stock solution was divided into 1 mL aliquots, 5-10 mg biocatalyst was added and the reactions warmed in an orbital shaker thermostatted at 40° C. and 300 rpm. The reactions were followed by reverse phase HPLC, and reactions which showed an acceptable degree of conversion were repeated at 100 mg/ml concentration. Biocatalysts which showed promising activity are listed below. All enzymes which catalysed hydrolysis were (S)-selective.

| Biocatalyst | Conversion @ 4 days (%) | e.e. (S)-Acid product (%) |
|---|---|---|
| *Mucor miehei* lipase (Lipozyme RM) | 50 | 60 |
| *Mucor miehei* lipase (Roche L-9 C-2 supported) | 15 | — |
| *Candida rugosa* lipase | 15 | — |
| *Rhizopus oryzae* lipase | 15 | — |
| *Thermomyces lanuginosa* lipase (NovoTL100) | 25 | — |
| *Rhizopus delmar* lipase | 15 | — |
| *Mucor javanicus* lipase | 15 | — |
| *Pseudomonas cepacia* on Celite (Amano PS-C) | 15 (1 day) | — |
| *Pseudomonas cepacia* CLEC | 40 (1 day) | 92 |
| *Pseudomonas cepacia* (Amano PS-S powder) | 29 (1 day) | 100 |

Example 15

Resolution of Racemic Ethyl Thioester Using *Pseudomonas cepacia* Lipase PS-S

Racemic S-Ethyl 2-{[2-(4-hydroxyphenyl)ethyl]thio}-3-[4-(2-{4-[(methylsulfonyl)oxy]-phenoxy}ethyl)phenyl]propanethioate (20 mg) was dissolved in 9:1 tert-butanol (t-BuOH)-water and lipase PS-S added (4 mg). The reaction was warmed to 40° C. in an orbital shaker at 300 rpm. The reaction was monitored by reverse phase and chiral HPLC. After 18 hours, the conversion of Ester to Acid was 29%, providing Acid in 100:0 (S)—(R) ratio. An aliquot of trioctylamine (15 μL) was added to racemise the residual ester and the reaction monitoring continued. After a further 48 hours, the conversion of Ester to Acid was 72%, again providing Acid in 100:0 (S):(R) ratio. A further portion of trioctylamine (15 μL) was added. After a further 18 hours, conversion of Ester to Acid was ~80% providing Acid in 100:0 (S):(R) ratio.

Example 16a

Deracemisation of racemic S-Ethyl 2-{[2-(4-hydroxyphenyl)ethyl]thio}-3-[4-(2-{4-[(methylsulfonyl)oxy]phenoxy}ethyl)phenyl]propanethioate using *Pseudomonas cepacia* CLEC and *Pseudomonas cepacia* on ceramic Racemic S-Ethyl 2-{[2-(4-hydroxyphenyl)ethyl]thio}-3-[4-(2-{4-[(methylsulfonyl)oxy]-phenoxy}ethyl)phenyl]propanethioate (200 mg) was dissolved in 9:1 t-BuOH-water (4 mL). To this solution was added trioctylamine (48.3 μL). This solution was divided into 1 mL aliquots.

To one vessel was added *Pseudomonas cepacia* CLEC (11 mg); to a second was added *Pseudomonas cepacia* on ceramic particles (Amano PS-C) (40 mg). A third vessel was maintained as control with no addition of biocatalyst to assess the rate of background hydrolysis. The reactions were placed in an orbital shaker thermostatted at 38° C. and 300 rpm. At day 6, a further portion of trioctylamine (15 μL) was added to each reaction. The reactions were monitored by reverse phase and chiral HPLC.

| | | 4 hours | 18 hours | 2 days | 6 days | 8 days |
|---|---|---|---|---|---|---|
| Control | Conversion (%) | — | — | — | — | — |
| CLEC PC | Conversion (%) | 5 | 20 | 33 | 62 | 75 |
| | E.R. Acid (S):(R) | | 100:0 | 100:0 | 100:0 | 99.25:0.75 |
| | E.R. Ester (S):(R) | | 49:51 | 40:60 | 30:70 | 50:50 |
| PS-C | Conversion (%) | trace | 3 | 7 | 20 | 25 |
| | E.R. Acid (S):(R) | | 100:0 | 100:0 | 100:0 | 100:0 |
| | E.R. Ester (S):(R) | | 44:56 | 49:51 | 49:51 | 50:50 |

Example 16b

Deracemisation of racemic S-Ethyl-2-{[2-(4-hydroxyphenyl)ethyl]thio}-3-[4-(2-{4-[(methylsulfonyl)oxy]phenoxy}ethyl)phenyl]propanethioate using *Pseudomonas cepacia* powder Racemic S-Ethyl 2-{[2-(4-hydroxyphenyl)ethyl]thio}-3-[4-(2-{4-[(methylsulfonyl)oxy]-phenoxy}ethyl)phenyl]propanethioate (20 mg) was dissolved in 9:1 t-BuOH-water (1 mL). To this solution was added *Pseudomonas cepacia* lipase powder (5 mg, Amano PS-S). The reaction was placed in an orbital shaker thermostatted at 38° C. and 300 rpm. After 18 hours, trioctylamine (15 μL, 34.2 μmol) was added. After 3 days, a further portion of trioctylamine was added; and again on day 6. The reactions were monitored by reverse phase and chiral HPLC.

| time (days) | conversion (%) | E.R. Acid (S):(R) | E.R. Ester (R):(S) |
|---|---|---|---|
| 0.75 | 29 | 100:0 | 68.5:31.5 |
| 3 | 73 | 100:0 | 78.5:21.5 |
| 4 | 80 | 100:0 | 60:40 |

Example 17

Transesterification of Racemic S-Ethyl 2-{[2-(4-hydroxyphenyl)ethyl]thio}-3-[4-(2-{4-[(methylsulfonyl)oxy]phenoxy}ethyl)phenyl]propanethioate Racemic S-Ethyl 2-{[2-(4-hydroxyphenyl)ethyl]thio}-3-[4-(2-{4-[(methylsulfonyl)oxy]-phenoxy}ethyl)phenyl]propanethioate (20 mg) was dissolved in 1:1 tert-Butyl methyl ether:n-Butanol (1 mL; +3% water, +catalytic trioctylamine). To this solution was added either *Pseudomonas cepacia* CLEC or *Pseudomonas cepacia* on ceramic particles (Amano PS-C). The reaction was placed in an orbital shaker thermostatted at 38° C. and 300 rpm. The reactions were monitored by reverse phase and chiral HPLC. After 14 days, the corresponding Butyl Oxoester was produced in 76% and 60% conversion respectively, and >95:5 e.r.; some Acid was also produced in ~10% yield and 100:0 e.r.

The invention claimed is:

1. A process for the preparation of an enantiomerically enriched compound of formula I and pharmaceutically acceptable salts thereof

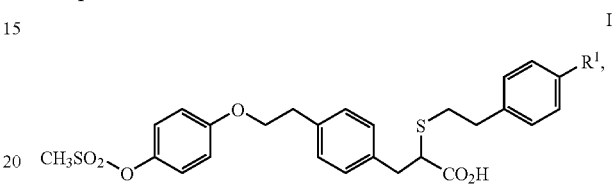

in which $R^1$ represents chloro, fluoro, or hydroxy;

which comprises hydrolysing a compound of formula II

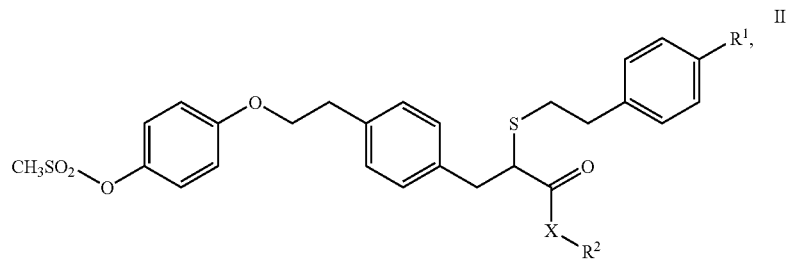

in which $R^1$ is as initially defined;

X is O or S; and, $R^2$ is a $C_{1-10}$alkyl group, a $C_{1-6}$haloalkyl, a $C_{2-6}$alkenyl group, an aryl, or an aryl$C_{1-6}$alkylene group, with or without additional hetero substitution;

with a lipase selected from the group consisting of (a) *Mucor miehei* lipase, *Candida rugosa* lipase, *Candida cylindracia* lipase, *Thermomyces lanuginosa* lipase, *Mucor javanicus* lipase, and *Rhizopus delemar* lipase, when X is O; and, (b) *Pseudomonas cepacia* lipase, when X is S;

in the presence of a reaction medium at a temperature in the range of 10-60° C.

2. A process for the preparation of an enantiomerically enriched compound of formula I and pharmaceutically acceptable salts thereof

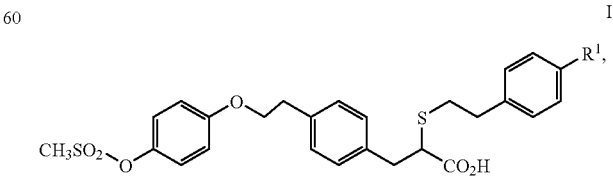

in which R¹ represents chloro, fluoro, or hydroxy;
which comprises hydrolysing a compound of formula II

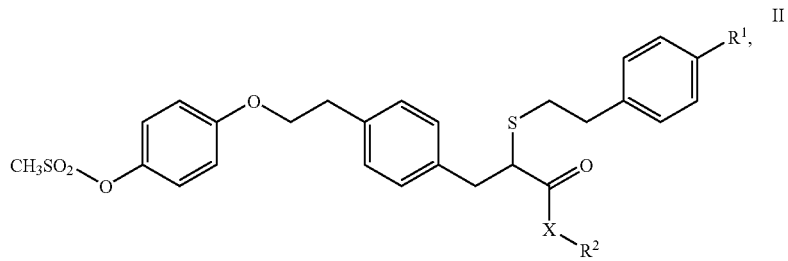

in which R¹ is as initially defined;
X is O; and,
R² is a $C_{1-10}$alkyl group;
with a lipase selected from the group consisting of *Mucor miehei* lipase, *Candida rugosa* lipase, *Candida cylindracia* lipase, *Thermomyces lanuginosa* lipase, *Mucor javanicus* lipase, and *Rhizopus delemar* lipase, in the presence of a reaction medium.

3. A process for the preparation of an enantiomerically enriched compound of formula I or a pharmaceutically acceptable salt thereof

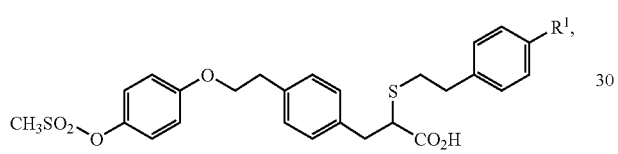

I in which R¹ represents chloro, fluoro, or hydroxy;
which comprises hydrolysing a compound of formula II

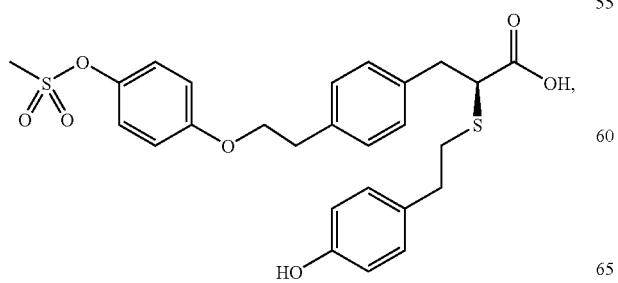

II in which R¹ is as initially defined;
X is S; and,
R² is a $C_{1-10}$alkyl group;
with *Pseudomonas cepacia* lipase in the presence of a reaction medium.

4. A process for the preparation of a compound of formula III or a pharmaceutically acceptable salt thereof

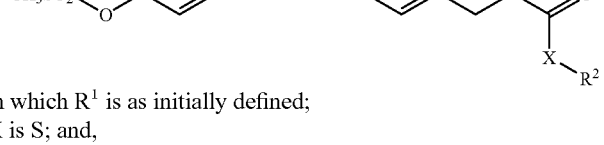

III comprising hydrolysing a compound of formula IV

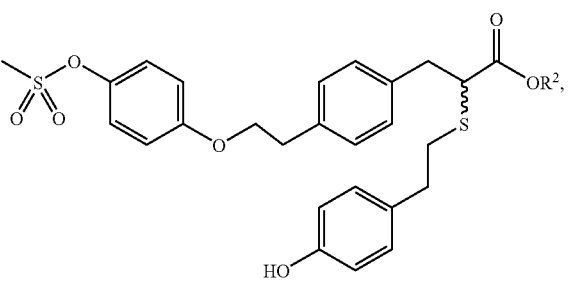

IV in which R² is a $C_{1-10}$alkyl group, a $C_{1-6}$haloalkyl, a $C_{2-6}$alkenyl group, an aryl, or an aryl$C_{1-6}$alkylene group, with or without additional hetero substitution;
with a lipase selected from the group consisting of *Mucor miehei* lipase, *Candida rugosa* lipase, *Candida cylindracia* lipase, *Thermomyces lanuginosa* lipase, *Mucor javanicus* lipase, and *Rhizopus delemar* lipase, in a reaction medium.

5. A process for the preparation of a compound of formula III or a pharmaceutically acceptable salt thereof

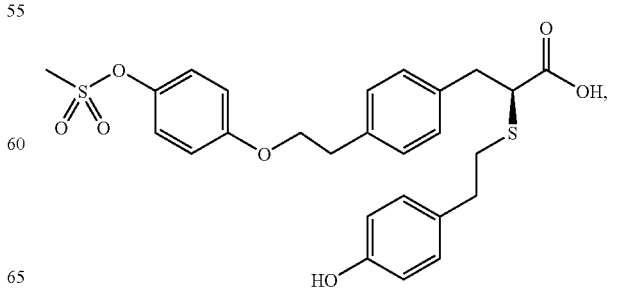

III comprising hydrolysing a compound of formula V

V

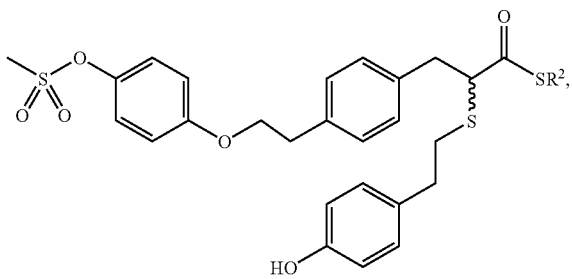

in which $R^2$ is a $C_{1-10}$alkyl group, a $C_{1-6}$haloalkyl, a $C_{2-6}$alkenyl group, aryl or an aryl$C_{1-6}$alkylene group, with or without additional hetero substitution;
with *Pseudomonas cepacia* lipase in a reaction medium.

6. A process for the preparation of a compound of formula I which comprises,
   (a) reacting a compound of formula VI

VI

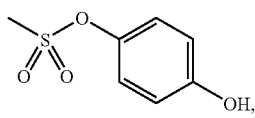

with a compound of formula VII

VII

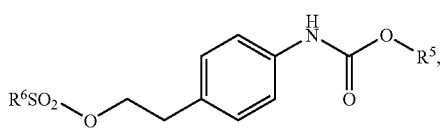

in which $R^5$ represents a $C_{1-6}$alkyl group; and,
$R^6$ represents p-tolyl in an inert solvent;
in the presence of a base at a temperature in the range of 0° to 150° C. to give a compound of formula VIII

VIII

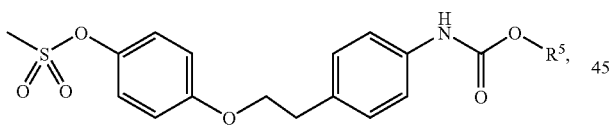

in which $R^5$ is as initially defined;
(b) reacting a compound of formula VIII with an acid HA, wherein HA represents HCl, HBr, or trifluoroacetic acid to give a salt of formula IX

IX

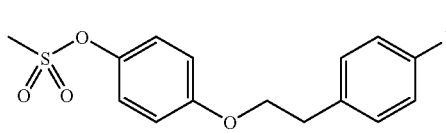

in which HA is as initially defined;
(c) diazotising a compound of formula IX in the presence of hydrochloric acid to give a diazonium salt solution at a temperature in the range of −5° C. to 10° C.; and,
reacting the diazonium salt solution with acrylic acid in an aqueous reaction medium, optionally in the presence of a catalyst; and, reacting the product obtained with ammonia to give a compound of formula X

X

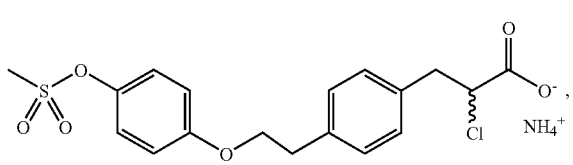

(d) reacting a compound of formula X with an acid and then with an alcohol of formula $R^2$OH, optionally in the presence of a water scavenging system to give a compound of formula XI,

XI

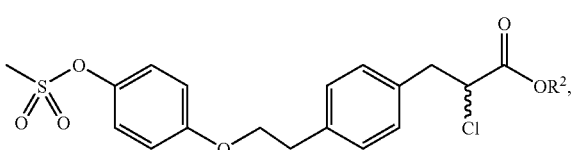

in which $R^2$ is a $C_{1-10}$alkyl group, a $C_{1-6}$haloalkyl, a $C_{2-6}$alkenyl group, an aryl, or an aryl$C_{1-6}$alkylene group, with or without additional hetero substitution;
(e) reacting the ester of formula XI with a compound of formula XII

XII

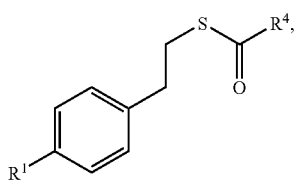

in which $R^1$ is chloro, fluoro, or hydroxy; and,
$R^4$ is methyl or phenyl;
in the presence of a base to give a compound of formula XIII

XIII

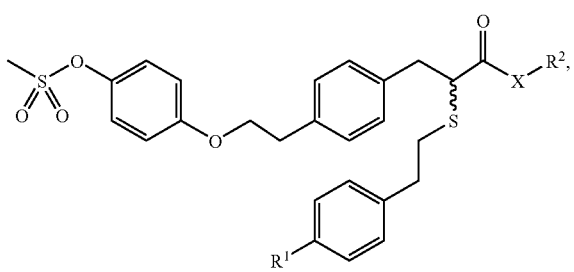

in which $R^1$ and $R^2$ are as initially defined, and X is O; and,
(f) hydrolysing a compound of formula XIII with a lipase selected from the group consisting of
   (a) *Mucor miehei* lipase, *Candida rugosa* lipase, *Candida cylindracia* lipase, *Thermomyces lanuginosa* lipase, *Mucor javanicus* lipase, and *Rhizopus delemar* lipase;

in a suitable reaction medium at a temperature in the range of 10-50° C. to give a compound of formula I

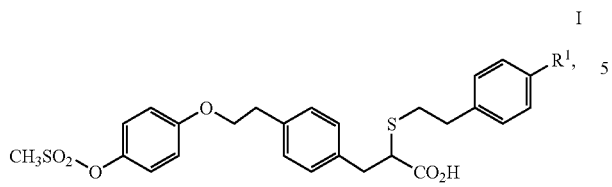

I which is enantiomerically enriched;
and,
(g) optionally reacting the compound of formula I with tert-butylamine in a suitable reaction medium to give the tert-butylammonium salt of the compound of formula I.

7. A telescoped process comprising,
(a) reacting a compound of formula X

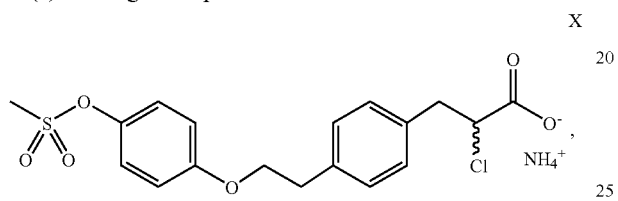

X with an acid and then with an alcohol of formula $R^2OH$ optionally in the presence of a water scavenging system to give a compound of formula XI

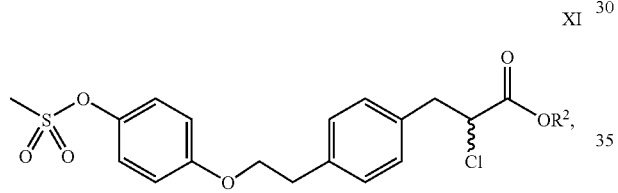

XI in which $R^2$ is a $C_{1-10}$alkyl group, a $C_{1-6}$haloalkyl, a $C_{2-6}$alkenyl group, an aryl, or an aryl$C_{1-6}$alkylene group, with or without additional hetero substitution;
(b) reacting the ester of formula XI with a compound of formula XII

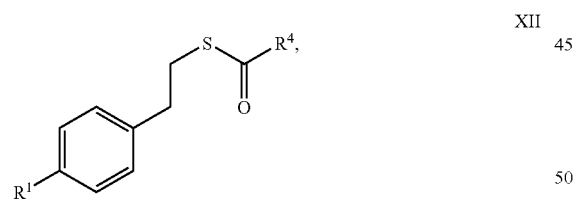

XII in which $R^1$ is chloro, fluoro, or hydroxy; and,
$R^4$ is methyl or phenyl;
in the presence of a base to give a compound of formula XIII

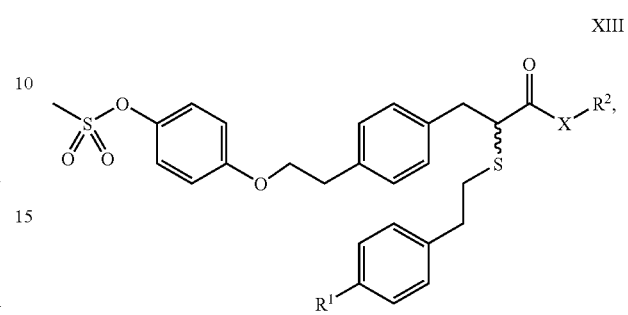

XIII in which $R^1$ and $R^2$ are as initially defined, and X is O; and,
(c) hydrolysing a compound of formula XIII with a lipase selected from the group consisting of
(a) *Mucor miehei* lipase, *Candida rugosa* lipase, *Candida cylindracia* lipase, *Thermomyces lanuginosa* lipase, *Mucor javanicus* lipase, and *Rhizopus delemar* lipase,
in a suitable reaction medium at a temperature in the range of 10-50° C. to give a compound of formula I

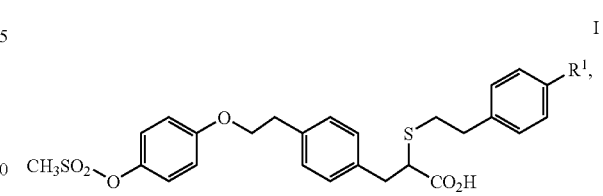

I which is enantiomerically enriched;
and,
(d) optionally reacting the compound of formula I with tert-butylamine in a suitable reaction medium to give the tert-butylammonium salt of the compound of formula I.

8. The method of claim 7, wherein in step (b), the base is methoxide.

* * * * *